US008835345B2

(12) United States Patent
Moores et al.

(10) Patent No.: US 8,835,345 B2
(45) Date of Patent: Sep. 16, 2014

(54) HYBRID CATALYSTS

(75) Inventors: Audrey Moores, Montreal (CA);
Ciprian M. Cirtiu, Quebec (CA)

(73) Assignee: The Royal Institution for the Advancement of Learning/McGill University, Montreal (CA)

(*) Notice: Subject to any disclaimer, the term of this patent is extended or adjusted under 35 U.S.C. 154(b) by 62 days.

(21) Appl. No.: 13/557,894

(22) Filed: Jul. 25, 2012

(65) Prior Publication Data
US 2013/0029835 A1 Jan. 31, 2013

Related U.S. Application Data

(60) Provisional application No. 61/512,055, filed on Jul. 27, 2011.

(30) Foreign Application Priority Data

Jul. 27, 2011 (CA) ..................................... 2747514

(51) Int. Cl.
*B01J 13/00* (2006.01)
*B01J 23/00* (2006.01)
*B01J 23/40* (2006.01)
*B01J 23/42* (2006.01)
*B01J 23/44* (2006.01)
*B01J 23/48* (2006.01)
*B01J 23/50* (2006.01)

(Continued)

(52) U.S. Cl.
CPC ................. *B01J 37/32* (2013.01); *C07C 2/861* (2013.01); *C07C 2523/44* (2013.01); *B01J 35/002* (2013.01); *B01J 35/0013* (2013.01); *B01J 23/42* (2013.01); *B01J 23/50* (2013.01); *B01J 23/462* (2013.01); *B82Y 40/00* (2013.01); *C07C 2523/42* (2013.01); *B01J 37/18* (2013.01); *B01J 35/06* (2013.01); *C07C 2523/46* (2013.01); *B01J 37/0201* (2013.01); *B01J 35/006* (2013.01); *C07C 2523/50* (2013.01); *B01J 23/755* (2013.01); *C07C 2523/755* (2013.01); *B01J 23/44* (2013.01); *B82Y 30/00* (2013.01); *B01J 21/18* (2013.01); *Y10S 977/773* (2013.01); *Y10S 977/775* (2013.01); *Y10S 977/778* (2013.01)
USPC ........... 502/159; 502/325; 502/327; 502/339; 502/347; 977/773; 977/775; 977/778; 516/9; 516/98; 516/106

(58) Field of Classification Search
USPC .......... 502/159, 325, 327, 339, 347; 977/773, 977/775, 778; 516/9, 98, 106
See application file for complete search history.

(56) References Cited

U.S. PATENT DOCUMENTS 7,776,777 B2 * 8/2010 Kim et al. ..................... 502/172

OTHER PUBLICATIONS

"Topochemical synthesis and catalysis of metal nanoparticles exposed on crystalline cellulose nanofibers," Hirotaka Koga et al. Chem. Commun., 2010, 46, pp. 8567-8569.*

(Continued)

*Primary Examiner* — Patricia L Hailey
(74) *Attorney, Agent, or Firm* — Goudreau Gage Dubuc; Isabelle Pelletier

(57) ABSTRACT

There is provided a catalyst comprising metal nanoparticles supported on nanocrystalline cellulose and a homogeneous catalyst system comprising this catalyst colloidally suspended in a fluid. There is also provided a method of producing this catalyst and various uses thereof.

19 Claims, 17 Drawing Sheets

(51) Int. Cl.
*B01J 31/00* (2006.01)
*B01F 3/00* (2006.01)
*B01F 17/00* (2006.01)
*C09K 3/00* (2006.01)
*B01D 21/01* (2006.01)
*C08J 3/02* (2006.01)
*C07C 2/86* (2006.01)
*B01J 35/00* (2006.01)
*B01J 23/46* (2006.01)
*B01J 35/06* (2006.01)
*B01J 37/02* (2006.01)
*B01J 23/755* (2006.01)
*B01J 37/32* (2006.01)
*B82Y 40/00* (2011.01)
*B01J 37/18* (2006.01)
*B82Y 30/00* (2011.01)
*B01J 21/18* (2006.01)

(56) References Cited

OTHER PUBLICATIONS

"Facile In Situ Synthesis of Noble Metal Nanoparticles in Porous Cellulose Fibers," Junhui He et al. Chem. Mater. 2003, 15, pp. 4401-4406.*
"Cellulose nanocrystallites as an efficient support for nanoparticles of palladium: application for catalytic hydrogenation and Heck coupling under mild conditions," Ciprian M. Cirtiu et al. Green Chemistry, 2011, 13, pp. 288-291.*
"Applications of functionalized and nanoparticle-modified nanocrystalline cellulose," Edmond Lam et al. Trends in Biotechnology, May 2012, vol. 30, No. 5, pp. 283-290.*
Araki, J. et al., "Flow properties of microcrystalline cellulose suspension prepared by acid treatment of native cellulose", Colloids and Surfaces A: Physicochemical and Engineering Aspects 142:75-82 (1998).
Bondeson, D. et al., "Optimization of the isolation of nanocrystals from microcrystalline cellulose by acid hydrolysis", Cellulose 13:171-180 (2006).
"Enantioselective GC Columns" Chiral Separations, N.p., 2011 Web Nov. 29, 2011. <http://chiral-separations.com/images/6/69/ApplicationGuide-ChiralSeparations_828.pdf>.
Cirtiu, C.M. et al., "Modification of the Surface Adsorption Properties of Alumina-Supported Pd Catalysts for the Electrocatalysis Hydrogenation of Phenol", Langmuir 22:6414:6421 (2006).
Cranston, E.D. & D.G. Gray, "Morphological and Optical Characterization of Polyelectrolyte Multilayers Incorporating Nanocrystalline Cellulose", Biomacromolecules 7:2522-2530 (2006).
Cyganiuk, A. et al., "Biotechnological fabrication of LaMnO3-carbon catalyst for n-butanol conversion of ketones", Carbon 48: 99-106 (2010).
Denisov, A.Y. et al., "Protein alignment using cellulose nanocrystals: practical considerations and range of application", J. Biomol NMR 47:195-204 (2010).
Dykeman, R.R. et al., "Enhanced Rate of Arene Hydrogenation with Imidazolium Functionalized Bipyridine Stabilized Rhodium Nanoparticles Catalysts", Inorg. Chem. 50:717-719 (2011).
Eichhorn, S.J. et al., "Review: Current international research into cellulosic fibres and composites", Journal of Materials Science 36:2107-2131 (2001).
Elazzouzi-Hafraoui, S. et al., "The Shape and Size Distribution of Crystalline Nanoparticles Prepared by Acid Hydrolysis of Native Cellulose", Biomacromolecules 9:57-65 (2008).
Ghanem, A., "Enantioselective Gas Chromatographic Separation of Racemic N-alkylated Barbiturates: Application of C11-Chirasil-Dex as Chiral Stationary Phase in GC" Analytical Chemistry Insights 2:75-80 (2007).
Habibi, Y. et al., "Cellulose Nanocrystals: Chemistry, Self-Assembly, and Applications", Chem. Rev. 110:3479-3500 (2010).
Hasani, M. et al., "Cationic surface functionalization of cellulose nanocrytals", Soft Matter 4:2238-2244 (2008).
Klemm, D. et al., "Cellulose: Fascinating Biopolymer and Sustainable Raw Material", Angew. Chem. Int. Ed. 44:3358-3393 (2005).
Klemm, D. et al., "Nanocelluloses: A New Family of Nature-Based Materials", Angew. Chem. Int. Ed. 50:5438-5466 (2011).
Klufers, P. & T. Kunte, "Palladium(II) Complexes of the Reducing Sugars D-Arabinose, D-Ribose, rac-Mannose, and D-Galactose", Chem. Eur. J. 9:2013-2018 (2003).
Lahiji, R.R. et al., "Atomic Force Microscopy Characterization of Cellulose Nanocrystals", Langmuir 26:4480-4488 (2010).
Liu, H. et al., "Selective Phenol Hydrogenation of Cyclohexanone Over a Dual Supported Pd-Lewis Acid Catalyst", Science 326:1250-1252 (2009).
Mahmoud, K.A. et al., "Cellusose Nanocrystal/Gold Nanoparticle Composite as a Matrix for Enzyme Immobilization", Applied Materials & Interfaces 1:1383-1386 (2009).
Marchessault, R.H. et al., "Some Hydrodynamic Properties of Neutral Suspensions of Cellulose Crystallites as Related to Size and Shape", Journal of Colloid Science 16:327-344 (1961).
Medrzycka, K.B., "The effect of particle concentration on zeta potential in extremely dilute solutions", Colloid Polym Sci 269:85-90 (1991).
Moon, R.J. et al., "Cellulose nanomaterials review: structure, properties and nanocomposites", Chem. Soc. Rev. 40:3941-3994 (2011).
Mukherjee, S.M. & H.J. Woods, "X-Ray and Electron Microscope Studies of the Degradation of Cellulose by Sulphuric Acid", Biochimica et Biophysica Acta 10:499-511 (1953).
Oksman, K., et al., "Manufacturing process of cellulose whiskers/polylactic acid nanocomposites", Composites Science and Technology 66:2776-2784 (2006).
Peng, B.L. et al., "Chemistry and Applications of Nanocrystalline Cellulose and its Derivatives: A Nanotechnology Perspective", The Canadian Journal of Chemical Engineering 89:1191-1206 (2011).
Pirkkalainen, K. et al., "Nanocomposites of magnetic cobalt nanoparticles and cellulose", Eur. Phys. J. D 49:333-342 (2008).
Reddy, K.R. et al., "Cellulose supported palladium(0) catalyst for Heck and Sonogashira coupling reactions", Journal of Molecular Catalysis A: Chemical 252:12-16 (2006).
Reddy, K.R. et al., "N-Arylation of nitrogen heterocycles with aryl halide and arylboronic acids catalyzed by cellulose supported by copper(0)", Journal of Molecular Catalysis A: Chemical 252:136-141 (2006).
Revol, J.-F. et al., "Solid Self-Assembled Films of Cellulose with Chiral Nematic Order and Optically Variable Properties", Journal of Pulp and Paper Science 24:146-149 (1998).
Revol, J.-F. et al., "Helicoidal self-ordering of cellulose microfibrils in aqueous suspension", Int. J. Biol. Macromol. 14:170-172 (1992).
Schurig, V., "Chiral separations using gas chromatography", Trends in Analytical Chemistry 21:647-661 (2002).
Shin, Y. et al., "Facile Stabilization of Gold-silver Alloy Nanoparticles on Cellulose Nanacrystal", J. Phys. Chem. C 112:4844-4848 (2008).
Shin, Y. et al., "Simple preparation and stabilization of nickel nanocrystals on cellulose nanocrystal", Materials Letters 61: 3215-3217 (2007).
Shin, Y. et al., "Synthesis and stabilization of selenium nanoparticles on cellulose nanocrystal", Materials Letters 61:4297-4300 (2007).
Talukdar, A.K. & K.G. Bhattacharyya, "Hydrogenation of phenol over supported platinum and palladium catalysts", Applied Catalysis A: General 96:229-239 (1993).
Xu, Y. et al., "Catalytic Performance of Cellulose Supported Palladium Complex for Heck Reaction in Water", Journal of Applied Polymer Science 110:2996-3000 (2008).

* cited by examiner

HYBRID CATALYSTS

CROSS REFERENCE TO RELATED APPLICATIONS

This application claims benefit, under 35 U.S.C. §119(e), of U.S. provisional application Ser. No. 61/512,055 and Canadian patent application no. CA 2 747 514, both filed on Jul. 27, 2011. All documents above are incorporated herein in their entirety by reference.

FIELD OF THE INVENTION

The invention relates generally to catalysts, uses thereof and a method of producing these catalysts. More specifically, the present invention is concerned with hybrid materials consisting of metal nanoparticles deposited onto colloidal cellulose nanocrystallites. Such materials can be used to catalyze hydrogenation reactions and Heck reactions.

BACKGROUND OF THE INVENTION

Cellulose is the most abundant organic renewable polymer available. Its structure consists of linear chains of (β)-1,4-linked anhydro-D-glucose units. Each of these units has three hydroxy groups available for functionalization. For wood pulp, the degree of polymerization (DP) can lie between 300 and 1700, with every unit corkscrewed 180° with respect to its neighbors:

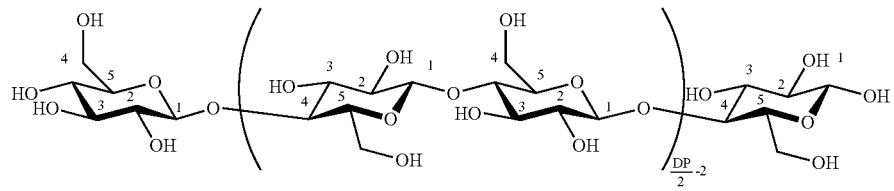

This structure provides cellulose polymer chain with extensive hydrogen-bonding possibilities as well as high chain stiffness.

In recent years, cellulose derivatives as well as other biopolymers have been studied as potentially efficient, cheap, renewable and biodegradable supports for catalysis, that is, heterogeneous catalysis, wherein the catalyst is normally solid (bulk catalyst) or can be supported on a solid support (supported catalysts) and the reactants are fluids (liquids or gases). For instance, hybrids made of bulk cellulose supporting Pd(0) and Cu(0) nanoparticles (NPs) proved active for the catalysis of C—C coupling reactions and of the N-arylation of nitrogen heterocycles respectively in organic solvents. Pd(II) complexes could also be stabilized onto cellulose and catalyze the Heck reaction in water. For homogeneous catalysis, the catalyst is in the same phase as the reactants, for example, all reactants and the catalyst are solubilized, dispersed or suspended in water. In other approaches, bulk cellulose was used as a precursor of microporous carbon supports for catalytic hybrids.

SUMMARY OF THE INVENTION

In accordance with the present invention, there is provided:
1. A catalyst comprising metal nanoparticles supported on nanocrystalline cellulose.
2. The catalyst of item 1, wherein the metal nanoparticles are comprised of at least one of the following metals: palladium, nickel, ruthenium, platinum, or silver.
3. The catalyst of item 2, wherein the metal nanoparticles are nickel nanoparticles.
4. The catalyst of item 2, wherein the metal nanoparticles are palladium nanoparticles.
5. The catalyst of any one of items 1 to 4, wherein the metal nanoparticles have a diameter size range from about 2 nm to about 10 nm.
6. The catalyst of item 5, wherein the metal nanoparticles have a diameter size range of about 2 nm to about 4 nm.
7. The catalyst of any one of items 1 to 6, wherein the loading of metal on the nanocrystalline cellulose is in a range of about 0.5 weight % to about 5 weight %.
8. The catalyst of any one of items 1 to 7, wherein the metal nanoparticles are uniformly distributed onto the nanocrystalline cellulose.
9. The catalyst of any one of items 1 to 8, wherein the nanocrystalline cellulose is cellulose nanocrystallites (CNCs).
10. The catalyst of any one of items 1 to 9, wherein the nanocrystalline cellulose is in the form of whiskers having a length in a range of about 100 nm to about 300 nm, and a width of about 5 nm to about 15 nm.
11. The catalyst of any one of items 1 to 10 being a catalytic hydrogenation catalyst.
12. The catalyst of item 11, wherein said hydrogenation is hydrogenation of phenol, 1-(2-methoxyphenyl)ethanone acetophenone, or alpha-tetralone.
13. The catalyst of any one of items 1 to 10 being a Heck coupling catalyst.
14. The catalyst of item 13, wherein the Heck coupling is Heck coupling of styrene and iodobenzene.
15. The catalyst of any one of items 1 to 10 being an enantioselective catalyst.
16. A homogeneous catalyst system comprising the catalyst of any one of items 1 to 15 colloidally suspended in a liquid.
17. The catalyst system of item 16, wherein the liquid is water, or an aqueous mixture of water and acetonitrile.
18. A method for producing the catalyst of any one of items 1 to 15, the method comprising:
   a. mixing an aqueous suspension of nanocrystalline cellulose with an acidic solution of a metal salt at a temperature of about 15° C. to about 25° C.; and
   b. exposing the resulting slurry to dihydrogen pressure in order to reduce the metal salt to a metal nanoparticle at a temperature of about 15° C. to about 25° C.
19. The method of item 18, wherein the mixing is performed by magnetic stirring, sonication, high speed mixing or a combination thereof.
20. The method of item 18 or 19, wherein the acidic solution of a metal salt is at a pH of about 2.
21. The method of any one of items 18 to 20, wherein the pressure is from about 2 to about 10 bars.

22. The method items 21, wherein the pressure is at about 4 bars.
23. The method of any one of items 18 to 22, wherein the metal salt is metal chloride.
24. The method of item 23, wherein the metal salt is palladium chloride or nickel chloride.
25. Use of a catalyst as defined in any one of items 1 to 10 for catalytic hydrogenation.
26. The use of item 25, wherein said hydrogenation is hydrogenation of phenol, 1-(2-methoxyphenyl)ethanone acetophenone, or alpha-tetralone.
27. Use of a catalyst as defined in any one of items 1 to 10 for catalyzing a Heck coupling.
28. The use of item 27, wherein the Heck coupling is Heck coupling of styrene and iodobenzene.

BRIEF DESCRIPTION OF THE DRAWINGS

In the appended drawings.

DETAILED DESCRIPTION OF THE INVENTION

Turning now to the invention in more details, there is provided a catalyst comprising metal nanoparticles supported on nanocrystalline cellulose. Advantageously, there is also provided a homogeneous catalyst system comprised of a catalyst comprising metal nanoparticles supported on nanocrystalline cellulose colloidally suspended in a liquid, such as water or an aqueous mixture of water and acetonitrile.

Above, "colloidally suspended" means that the catalyst and the fluid form two phases that are microscopically dispersed. The catalyst is evenly distributed throughout the fluid. The catalyst forms the internal phase while the fluid is the medium phase.

In embodiments, the metal nanoparticles are comprised of at least one of the following metals: palladium, nickel, ruthenium, platinum, or silver. In embodiments, they have a diameter size range from about 2 nm to about 10 nm, more specifically from about 2 nm to about 4 nm.

In embodiments, the metal nanoparticles are uniformly distributed onto the nanocrystalline cellulose. An example of such uniform distribution can be seen in FIG. 6.

In embodiments, the metal nanoparticles are palladium nanoparticles. In embodiments, the nanoparticles are monodisperse. In embodiments, they have a diameter size range of about 2 nm to about 4 nm. In embodiments, the loading of palladium in the nanocrystalline cellulose is in a range of about 0.5 weight % to about 5 weight %.

In embodiments, the metal nanoparticles are nickel nanoparticles.

The term "nanocrystalline cellulose" as used herein means celluloses in the form of nanocrystals, i.e. crystals having a size in the nanometer range. Examples of nanocrystalline cellulose include cellulose nanocrystallites (CNC), cellulose nanocrystals, and cellulose whiskers. In embodiments, the nanocrystalline cellulose is cellulose nanocrystallites.

Figure 1:
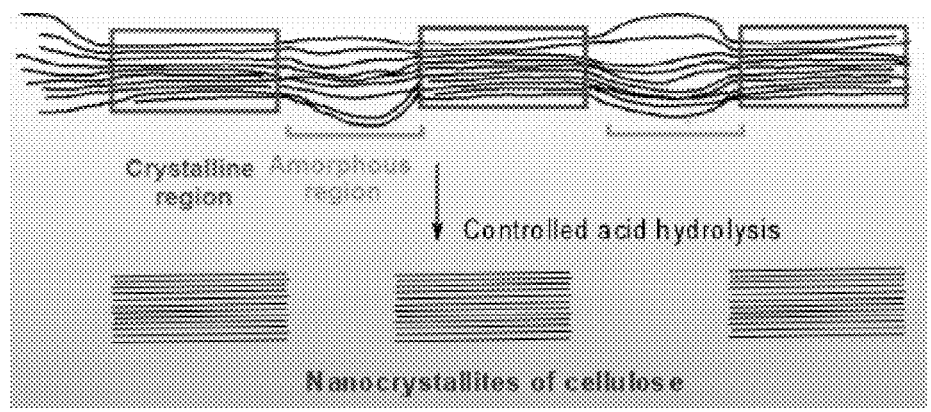
FIG. 1 shows the crystalline and amorphous regions of cellulose microfibrils and the production of nanocrystallites of cellulose by controlled acid hydrolysis.

Within the wood cell walls, Van der Waals forces and hydrogen bonding promote parallel stacking of cellulose chains to form elementary fibrils, which grow to form microfibrils. These ensembles of cellulose chains are composed of two main regions, crystalline and amorphous. Crystalline sections consist of tightly packed ordered cellulose chains stabilized by a strong hydrogen-bonding network and Van der Waals forces. The amorphous regions are less organized sections where internal strain causes the cellulose microfibrils to tilt and twist. They occur periodically between crystalline regions and can be removed by acid hydrolysis to yield rod-like cellulose nanocrystallites (CNC) residues with distinct properties (see FIG. 1).

These nanocrystallites have distinct properties such as low cost, availability, renewability, lightweight, nanoscale dimension, high surface area, biodegradability, a unique morphology, a well-defined size and morphology, a controlled surface chemistry, superior mechanical strength and high crystalline order, which bulk, or microcrystalline cellulose does not possess. Indeed, CNCs are nano-bundles, or nano-whiskers, generally of about 100 to 250 nm long by 3-10 nm with axial physical properties approaching those of perfect crystals. The surface of CNC has been described as a smooth surface featuring hydroxyl groups and negatively charged sulfate ester groups, conferring a good colloidal stability in water. CNCs can be produced at the semi-industrial scale.

In embodiment, the nanocrystalline cellulose has a length in a range of about 100 nm to about 300 nm, and a width of about 5 nm to about 15 nm.

As shown in the Examples below, the catalyst and catalyst system can be used in hydrogenation reactions including the hydrogenation of phenol. Also, the catalyst and catalyst system can be used in Heck coupling, including the Heck coupling of styrene and iodobenzene. In particular, the catalyst and catalyst system were observed to be enantioselective. It is important to note this use of a non-modified, naturally occurring chiral compound to induce chirality into a molecule during catalysis. This differs from other known systems where the chiral inducer is grafted or added to the system.

Figure 12:
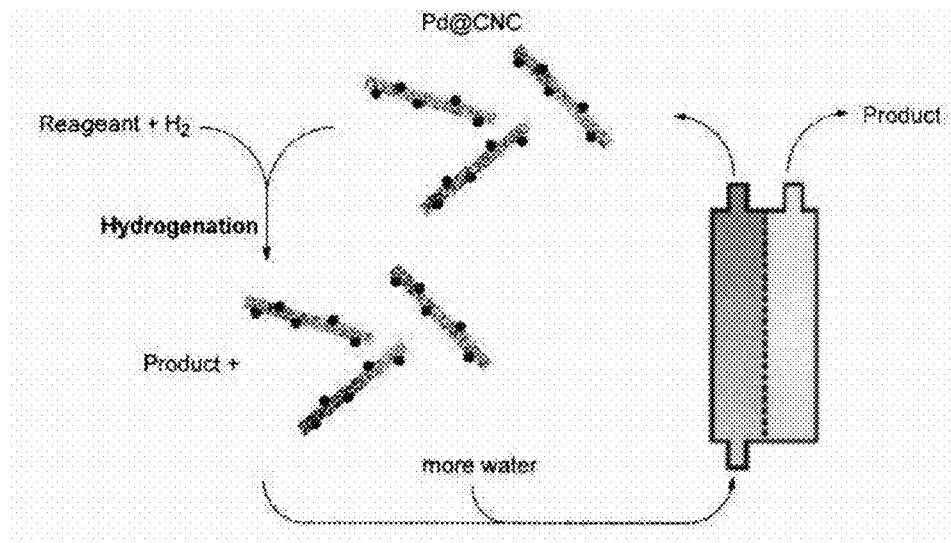
FIG. 12 is a scheme showing the recycling of Pd@CNC by dialysis.

The catalyst of the invention can also be separated and recovered (i.e. recycled), which is economically advantageous. This can be achieved by dialysis as shown in FIG. 12.

There is also provided a method for producing the above catalyst. The method comprises: mixing an aqueous suspension of nanocrystalline cellulose with an acidic solution of a metal salt at a temperature of about 15° C. to about 25° C.; and exposing the resulting slurry to dihydrogen pressure in order to reduce the metal salt to a metal nanoparticle at a temperature of about 15° C. to about 25° C. The mixing can be performed by magnetic stirring, sonication, high speed mixing or a combination thereof. The acidic solution of a metal salt can be at a pH of about 2. The pressure can be at about 2 to 10 bars, for example 4 bars. The metal salt can be a metal chloride, such as palladium chloride.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

This invention is not limited in its application to the details of construction and the arrangement of components set forth in the following description or illustrated in the drawings. The invention is capable of other embodiments and of being practiced or of being carried out in various ways.

The present invention is illustrated in further details by the following non-limiting examples.

Example 1

Figure 2:
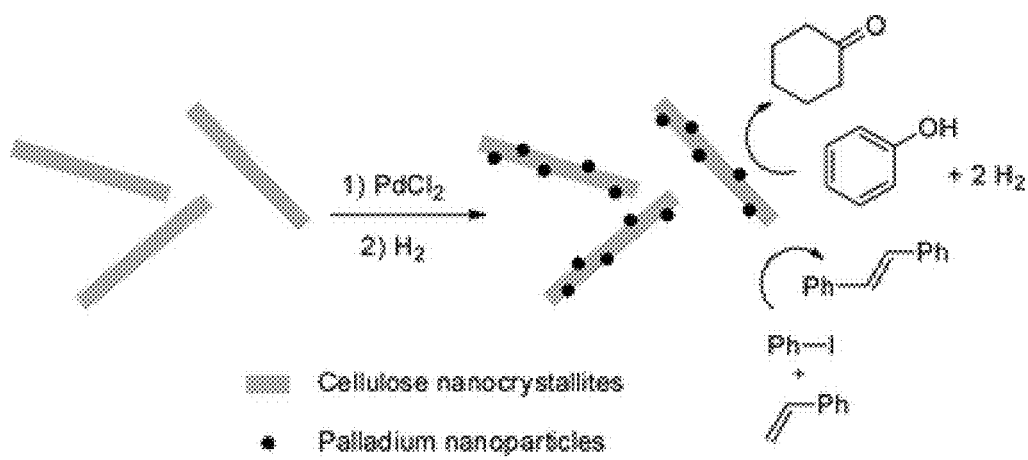
FIG. 2 is a scheme of the synthesis of PdNPs@CNCs, catalytic hydrogenation of phenol under dihydrogen pressure and Heck coupling of styrene and iodobenzene.

Below is presented the successful synthesis of an embodiment of the catalyst of the invention: Pd NPs deposited onto nanocrystalline cellulose (PdNPs@CNCs) under mild conditions and its application for the catalytic hydrogenation of phenol under very mild conditions in water as a solvent as well as for the Heck coupling of styrene and iodobenzene at low temperature in a water-acetonitrile, 1:1 mixture (FIG. 2).

CNCs synthesised by acid hydrolysis of wood pulp were provided by FPInnovations. 50 mL of an acidic solution (pH adjusted at 2 with HCl) of $PdCl_2$ ($1.5 \times 10^{-3}$ M) was mixed with a suspension of 500 mg of CNCs in 50 mL HCl solution at pH 2 and left under magnetic stirring for 10 min to homogenize the suspension. The final concentration in $PdCl_2$ was $0.75 \times 10^{-3}$ M while the CNCs concentration in the mixture was 0.5% w/w. Then, the mixture was placed under $H_2$ pressure (4 bars) in a PARR multiple-reactor system for 2 hours. The obtained catalyst PdNPs@CNCs solution was simply diluted with water and transferred into another reactor for the hydrogenation reaction of phenol. Prior to TGA, FTIR, and Inductive Coupled Plasma (ICP) analyses, the suspension was decanted to remove the potential palladium loss and then freeze dried. The catalytic tests were performed with 14.5 mL of PdNPs@CNCs suspension (which contains 40 mg of CNCs) and 0.5 mL phenol solution (at 2.5 mg $mL^{-1}$) to reach a phenol concentration in reactor of $8.85 \times 10^{-4}$ M. Two blank samples were prepared and compared to the PdNPs@CNCs catalyst. The first was obtained by reducing the $PdCl_2$ solution under $H_2$ pressure (4 bars) for 2 h in absence of CNCs. The second was obtained by subjecting the CNCs suspension to $H_2$ pressure (4 bars) for 2 hours in absence of Pd precursor. In a general procedure for the Heck coupling, styrene (0.24 mmol), iodobenzene (0.2 mmol) and $K_2CO_3$ (0.4 mmol) were mixed in 5 mL $CH_3CN$. Then 5 mL of the aqueous solution containing the freshly prepared catalyst (25 mg PdNPs@CNCs) was added and stirred at a temperature of 100° C. A blank experiment was carried out in the absence of catalyst and no conversion was observed.

Quantification for the catalytic hydrogenation and Heck coupling was done by gas chromatography-mass spectroscopy (GC-MS). Infrared spectra were recorded on a Spectrum BX Perkin Elmer instrument equipped with a diamond crystal Attempted Total Reflectance (ATR) accessory and a deuterated triglycine sulphate (DTGS) detector. All spectra were collected with a resolution of 4 $cm^{-1}$ in the range 4000-550 $cm^{-1}$. Thermogravimetric analyses were conducted on a Q500 equipment from TA Instruments with a linear heating rate of 10° C. $min^{-1}$ under a constant $N_2$ flow (40 mL $min^{-1}$). X-Ray photoelectron spectra (XPS) were obtained for the freeze-dried catalysts on an Escalab 220i XL instrument from VG equipped with a hemispherical analyzer and an Al anode (monochromatic Kα X-rays at 1486.6 eV) used at 12 kV and 20 mA. Spectra were obtained at room temperature and the operating pressure in the analysis chamber was below $10^{-9}$ Torr. The binding energies of the photoelectrons were calibrated by the aliphatic adventitious hydrocarbon C(1s) peak at 284.6 eV. Transmission electron microscopy (TEM) pictures were obtained using a JEOL JEM 2100-F instrument operated at 200 kV. The TEM grid containing bare CNCs was stained with 4% uranyl acetate prior to drying and analysis.

Figure 3:
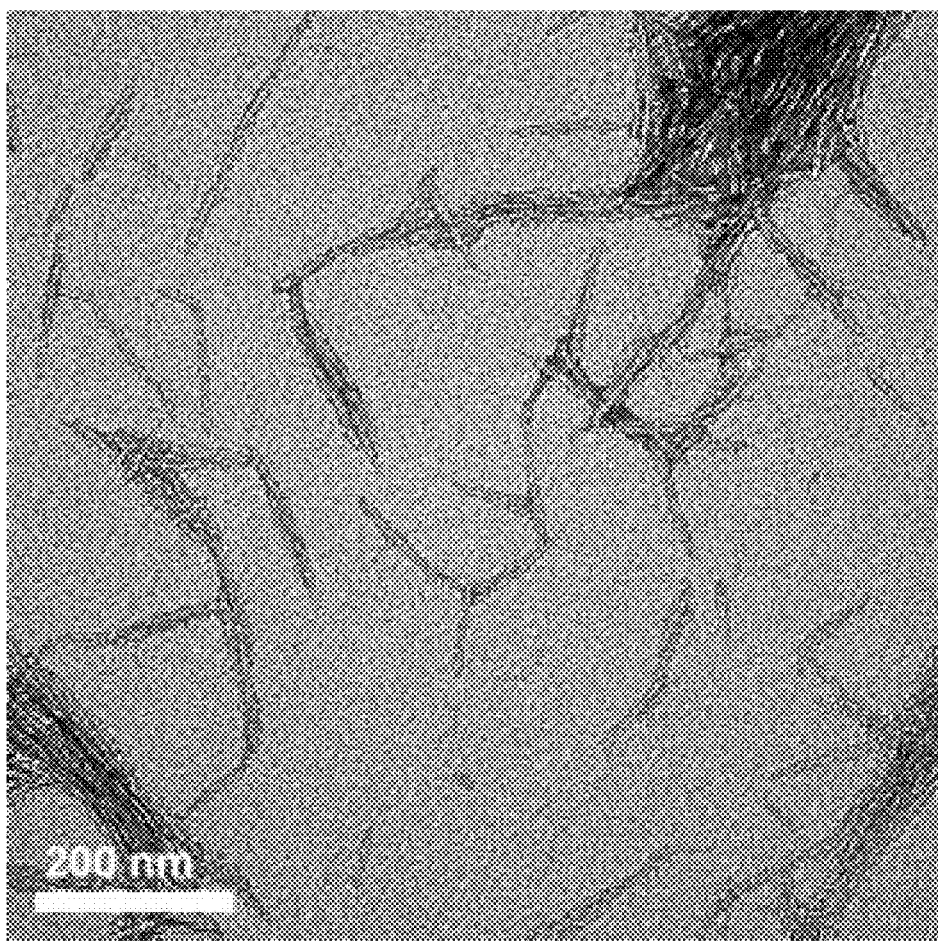
FIG. 3 shows a Transmission Electron Microscopy (TEM) micrograph of CNCs negatively stained with 4% uranyl acetate (scale bar: 200 nm)
Figure 6:
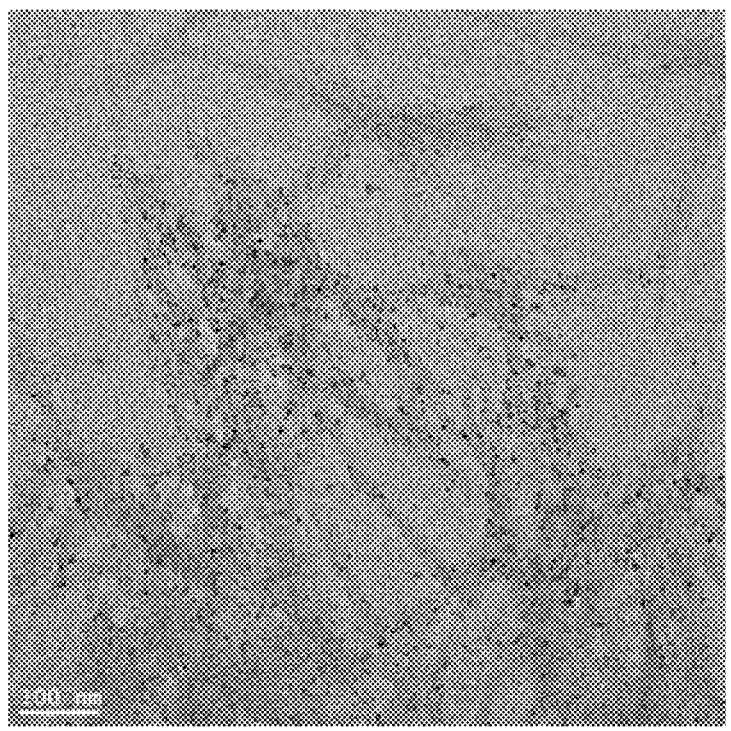
FIG. 6 shows a TEM picture of unstained PdNPs@CNCs sample (scale bar: 100 nm)

CNCs morphology was analyzed by TEM which confirmed they exist as whiskers (FIG. 3) of about 150 nm in length and about 5 nm width, as described before. Negative staining with uranyl acetate allowed each individual whisker to be seen clearly either as single rods or in larger agglomerates. Uranyl staining was not used to analyze the Pd@CNC to ensure unambiguous characterization of palladium nanoparticles (FIG. 6).

Figure 4:
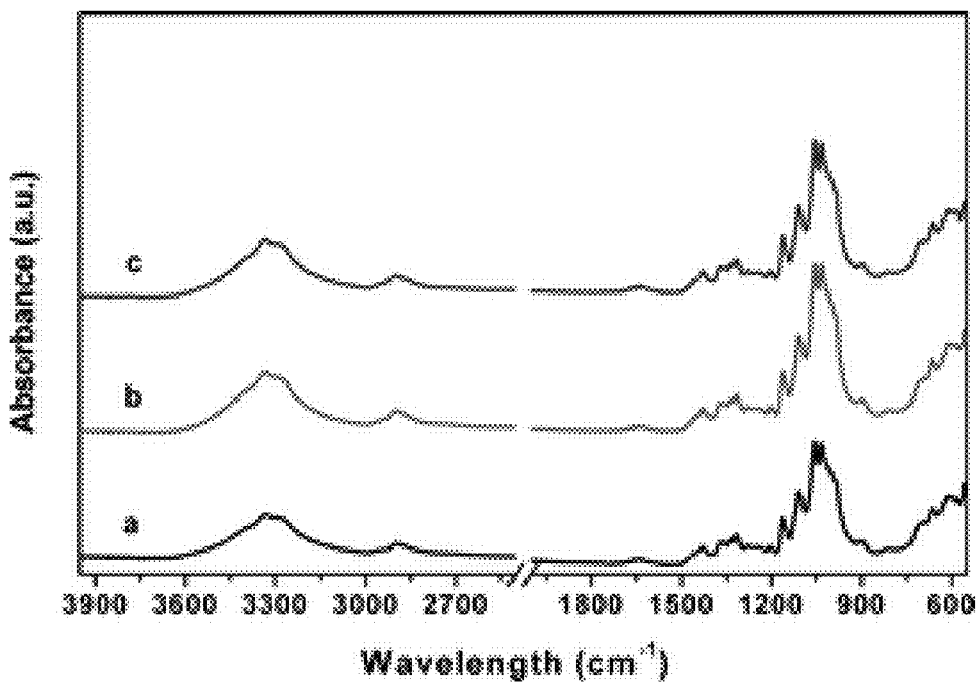
FIG. 4 is a (Fourier-Transformed Infrared) FTIR spectra obtained from CNCs before (a) and after exposure to hydrogen pressure in solid form (b) and in acidified solution (c)

Thermal, chemical and colloidal stabilities under the conditions of both the hybrid synthesis and catalysis were tested. Aqueous suspensions of CNCs were exposed to 10 bars of $H_2$, as well as acidic conditions (pH 1). Dried samples of CNCs were also exposed to 10 bars of $H_2$ and 150° C. In all cases, no change in the FT-IR spectra (FIG. 4) was indicative of chemical stability under the above-mentioned conditions. The colloidal stability of a homogeneous suspension of CNCs (0.1% w/w) was estimated via zeta-potential surface-charge density measurements. A value of −32.59±1.42 mV was obtained, indicating a stable suspension, since positive or negative values higher than 30 mV are considered as such in the prior art.

Figure 5:
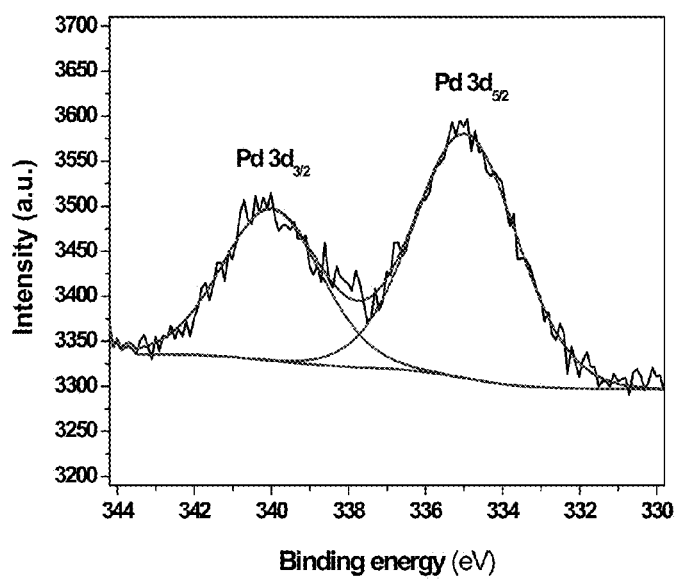
FIG. 5 shows an X-ray Photoelectron Spectrum (XPS) of Pd3d in PdNPs@CNCs.
Figure 7:
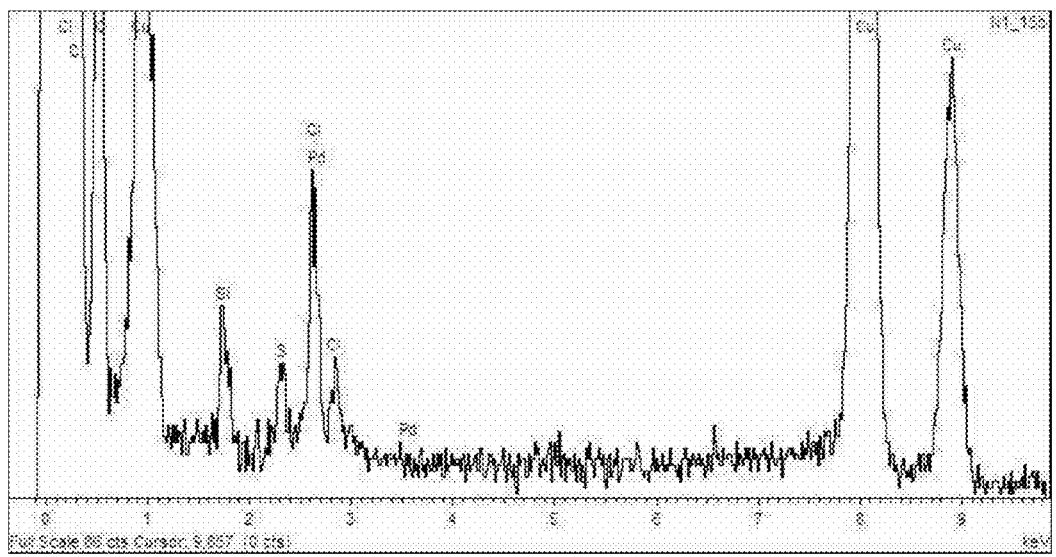
FIG. 7 shows an Energy Dispersive X-ray (EDX) analysis of PdNPs@CNCs nano-composite.
Figure 8:
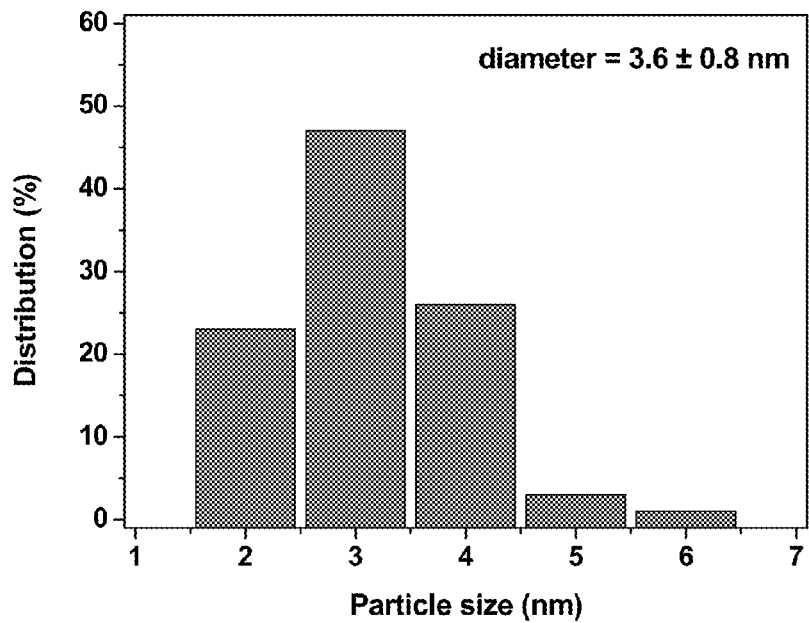
FIG. 8 shows the nanometer-scale size distribution for Pd nanoparticles deposited onto CNCs as obtained from TEM picture of FIG. 6.

Synthesis of PdNPs@CNCs was achieved in a two-step fashion. First a CNC suspension was mixed with a $PdCl_2$ aqueous solution at room temperature. The mixture instantly turned from pale yellow to pale brown, indicating coordination of the metal salts to the CNC surface. Then the resulting slurry was exposed to dihydrogen pressure (4 bars) for 2 hours at room temperature. Upon reduction, the solution turns dark gray, indicating the reduction of Pd(II) salts into Pd(0) nanoparticles, as confirmed by XPS analysis (FIG. 5). This reducing agent avoids formation of by-products other than HCl, thus simplifying the purification procedure. The crude sample was used for TEM and zeta-potential measurements, while the freeze-dried PdNPs@CNCs nano-composite was employed for the FTIR, TGA and XPS analyses. The TEM images (FIG. 6) of the non-stained nanocomposite revealed that surprisingly, a large number of Pd nanoparticles were formed and uniformly distributed onto the surface of CNCs after deposition. The EDX analysis confirmed that the darker spots on the micrograph are Pd nanoparticles with an average particles size of 3.6±0.8 nm (FIGS. 7 and 8). TEM also revealed that CNCs in the PdNPs@CNCs hybrid retained their "whisker" nature with limited aggregation. These features are believed to be the result of the very mild conditions of synthesis (room temperature) and the fact that the particles were kept in colloidal suspension, or freeze dried, if isolation as a powder was necessary. Additionally, in this synthesis, dihydrogen was used as a reducing agent, which did not degrade CNCs during the process. The new synthesized hybrid, PdNPs@CNCs, thus retained a high specific surface.

Figure 9:
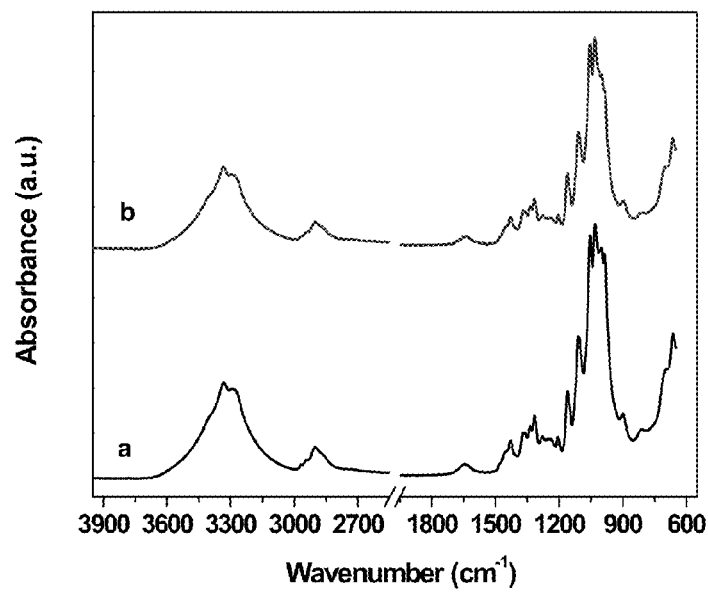
FIG. 9 shows FTIR spectra obtained from CNCs before (a) and after (b) deposition of PdNPs.

To confirm complete reduction of Pd(II) ions, XPS analysis was performed. The $Pd3d_{5/2}$ and $3d_{3/2}$ doublet located at 335.1 and 340.1 eV, respectively, were attributed to metallic Pd. Lack of peak at 336.5 eV, which is characteristic for Pd(II), confirmed the complete reduction of Pd(II) (FIG. 5). The Pd loading in PdNPs@CNCs catalyst was determined to be 0.5 wt % based on the ICP-AES analysis of the freeze-dried nano-composite. The integrity of CNCs was also checked by FTIR after Pd deposition and no structural change was measurable (FIG. 9). Surprisingly, the PdNPs@CNCs suspension maintained a good colloidal stability as reflected by a zeta-potential value of −41.97±6.75 mV.

Figure 10:
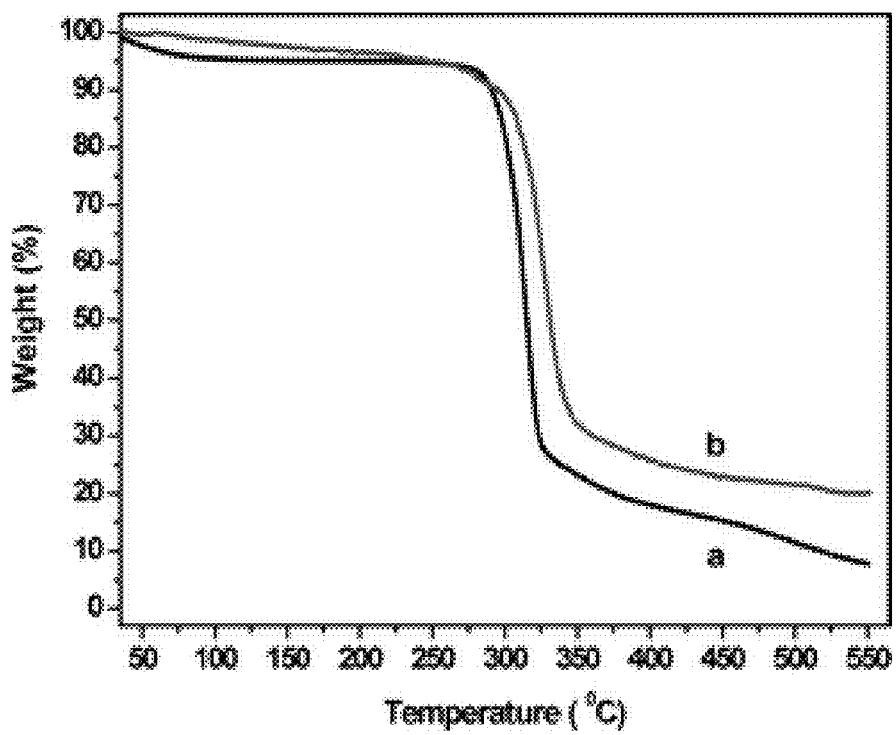
FIG. 10 shows Thermal Gravimetric Analysis (TGA) spectra of CNCs (a) and PdNPs@CNCs (b) under $N_2$ atmosphere.
Figure 11:
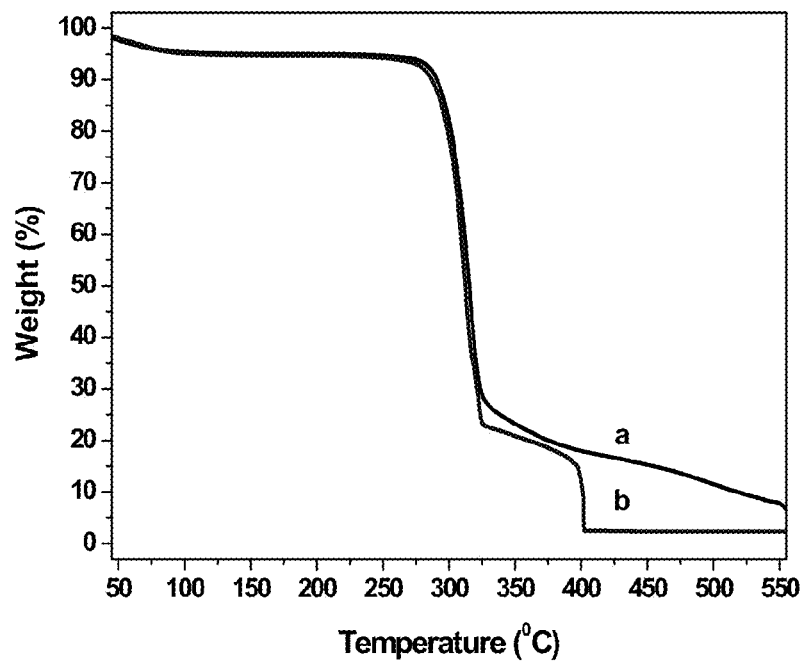
FIG. 11 shows the TGA spectra of CNCs under $N_2$ (a) and air (b) atmosphere.

Thermogravimetric analysis (FIG. 10) evidenced that deposition of Pd NPs onto CNCs did not alter the thermal behavior of CNCs, both the CNCs and PdNPs@CNCs decomposing above 275° C. under inert atmosphere. CNCs were also proved equally stable in an oxygen-containing atmosphere (FIG. 11), making them an attractive support for many catalytic reactions.

The catalytic activity of the newly synthesized PdNPs@CNCs was evaluated through the hydrogenation reaction of phenol. This catalytic reaction was chosen, because of its high economic importance, because of its dependence over the type of catalyst support used and also because phenol can be hydrogenated to cyclohexanone or further to cyclohexanol, bringing along a selectivity challenge. The reaction was carried out under very mild experimental conditions: moderate $H_2$ pressure (4 bars) and room temperature.

Table 1 presents the fraction of phenol converted to cyclohexanone in the catalytic hydrogenation reaction over various catalysts after 3 and 24 hours. Surprisingly, excellent conversion (90%) of phenol to cyclohexanone was obtained within the reaction time (24 hours) over the synthesized PdNPs@CNCs (entry 1).

It was verified that CNCs alone (entry 2) were inactive for this reaction. Also, palladium salts reduced under the same conditions in absence of CNCs (entry 3) were inactive.

The activity of PdNPs@CNCs was compared with the conversion obtained over various commercial catalysts, namely PdNPs@$Al_2O_3$, a non-suspendable solid typically produced by a polluting process, and PdNPs@C. 0.5% PdNPs@CNCs performed similarly to 1% PdNPs@$Al_2O_3$, which showed 100% conversion (entry 4). Thus, less of the catalyst was necessary (0.5% vs 1%) to obtain the same conversion.

Using even greater amounts of these commercial catalysts, namely 5% PdNPs@$Al_2O_3$ (entry 5) and 5% PdNPs@C (entry 6), performed poorly with 10% and 37% respectively.

The molar ratio phenol/Pd was kept fixed at 7/1 in all catalysts presented. Surprisingly, our catalyst proved 100% selective towards partial hydrogenation to cyclohexanone (FIG. 2). Both the synthesis of PdNPs@CNCs and the catalytic tests proved reproducible.

TABLE 1

Catalytic hydrogenation of phenol to cyclohexanone (room temperature, 4 bar of $H_2$)

| Entry | Catalyst (weight) | Phenol conversion (%) | |
|---|---|---|---|
| | | 3 h | 24 h |
| 1 | 0.5% PdNPs@CNCs (40 mg) | 36 | 90 |
| 2 | CNCs (40 mg) | 0 | 0 |
| 3 | Unsupported Pd (0.2 mg) | 0 | 0 |
| 4 | 1% PdNPs@$Al_2O_3$ (20 mg) | 44 | 100 |
| 5 | 5% PdNPs@$Al_2O_3$ (4 mg) | 0 | 10 |
| 6 | 5% PdNPs@C (4 mg) | 0 | 37 |

The catalytic activity of PdNPs@CNCs for a Heck coupling was assessed with styrene and iodobenzene as model substrates in a mixture of water-acetonitrile, 1:1 at 100° C. Using $K_2CO_3$ as a base, 75% of iodobenzene was converted in stilbene within 24 hours, at a molar ratio iodobenzene/Pd of 170/1. The good conversion obtained over 0.5% PdNPs@CNCs is comparable with that observed in the prior art (80%) over a cellulose supported Pd(0) catalyst with a Pd loading of 5% w/w, in an organic solvent, acetonitrile.

In summary, a novel nano-composite, PdNPs@CNCs, was obtained by reduction of $PdCl_2$ using dihydrogen allowing formation of Pd nanoparticles (average particles size 3.6±0.8 nm) uniformly distributed onto CNCs. This hybrid was successfully tested in the catalytic selective hydrogenation of phenol to cyclohexanone under mild experimental conditions (4 bar of $H_2$ and room temperature). Moreover, the catalyst has proved to be active for the Heck coupling of styrene and iodobenzene, with a conversion of 75% in a hydro-organic mixture. CNCs thus proved to be a good support for catalysis, with good thermal and chemical stability as indicated by TGA and FTIR analyses.

Example 2

Above, CNCs were demonstrated to be an effective support for catalysts. Palladium nanoparticles (Pd NPs) coated onto CNCs (PdNPs@CNCs) were indeed successfully tested during the hydrogenation of phenol as well as for the Heck coupling of styrene and iodobenzene. The catalyst can be recycled and reused several times for the Heck reaction in a mixture of water and acetonitrile. The present inventors have also observed that PdNPs@CNCs when used to catalyze the hydrogenation reaction of acetophenone, give an excellent conversion to 1-phenylethanol.

Herein below, two catalysts, PdNPs@CNCs and NiNPs@CNCs, were used to perform hydrogenation reactions on various pro-chiral substrates. The reactions were conducted in water, under $H_2$ pressure. The products were analyzed using a GC-MS instrument equipped with a chiral column. For PdNPs@CNCs, excellent conversion of 88.5% and 95.6% was achieved for 1-(2-methoxyphenyl)ethanone and alpha-tetralone, respectively. A novel catalyst, NiNPs@CNCs, was successfully tested for the first time during the hydrogenation of acetophenone and alpha-tetralone. Most importantly, enantioselectivity was achieved with two types of metal nanoparticles (Pd and Ni), demonstrating that CNCs are an effective support for enantioselective catalysis. Enantiomeric excesses of 29.4% and approximately 50% were achieved for 1-(2-methoxyphenyl)ethanol with PdNPs@CNCs and decahydronaphthalen-1-ol with NiNPs@CNCs, respectively.

CNCs were used as green catalyst supports for palladium (PdNPs@CNCs) and lower priced nickel nanoparticles (NiNPs@CNCs). Surprisingly, it is demonstrated herein that CNCs can achieve enantioselective catalysis. It is believed that the intrinsic chiral nature of the CNCs and the defined orientation of hydroxyl groups on the surface of the CNCs can be used to induce enantioselectivity. In fact, no matter the mechanism, the catalysts PdNPs@CNCs and NiNPs@CNCs were observed to be enantioselective.

Pro-chiral substrates with different functional groups and varying bulkiness were tested for enantioselective hydrogenation. These reactions were performed under different experimental conditions, namely temperature, pressure and reaction time. The products were studied using GC-MS equipped with a cyclodextrin chiral column, which enabled separation of enantiomers.

Experimental

Preparation of PdNPs@CNCs Catalyst

The $PdCl_2$ solution used to synthesize PdNPs@CNCs was prepared by dissolving $PdCl_2$ (50 mg) in distilled water (200 ml) in an Erlenmeyer flask. The mixture was sonicated for 1 h and stirred for 24 h. Additional $PdCl_2$ (20 mg) was added to saturate the solution and the mixture was stirred for 1 h. The brown solution was filtered using a vacuum filter. The brown residue was discarded and the yellow solution of $PdCl_2$ was kept to prepare the catalysts.

CNC (250 mg) was mixed with a pH 2 HCl solution (25 ml) in a 100 ml beaker. The $PdCl_2$ solution (24.75 ml) and 1M HCl (0.25 ml) were added. The solution was stirred on the magnetic stirrer and sonicated for 5 minutes each. The solution was placed in the PARR reactor for 2 h under $H_2$ pressure (4 bars) at room temperature.

Preparation of NiNPs@CNCs Catalyst

A $NiCl_2$ solution was first prepared by dissolving $NiCl_2$ (60 mg) into distilled water (250 ml). The solution was sonicated and stirred for 10 minutes each. The NiNPs@CNCs catalyst was prepared by combining CNC (250 mg) with pH 2 HCl (25 ml) in a 100 ml beaker. Freshly prepared $NiCl_2$ (24.75 ml) and 1M HCl (0.25 ml) were added. The solution was stirred on the magnetic stirrer and sonicated for 5 minutes each. The solution was placed in the PARR reactor for 2 h under $H_2$ pressure (4 bars) at room temperature.

Hydrogenation of Pro-Chiral Substrates with $H_2$ and PdNPs@CNCs

Hydrogenation of 1-(2-methoxyphenyl)ethanone and alpha-tetralone was performed using PdNPs@CNCs as a catalyst. Stock solutions of the substrates were prepared at different concentrations. The substrate (4 ml of the stock solution), PdNPs@CNCs (5 ml) and distilled water (6 ml) were mixed in a small vial. The solution was stirred for one minute on the vortex. A 1 ml aliquot was taken from the reaction mixture for GC analysis (T=0H). The mixture was placed in the PARR reactor for 2 h at room temperature under $H_2$ pressure (4 bars). A 1 ml aliquot of the reaction solution was mixed with 1 ml of the internal standard (cyclohexanol in ethyl ether). NaCl salt was added. The solution was stirred on the vortex for 15 seconds. A 1 ml aliquot was taken from the top layer and transferred to a GC vial (T=2H). The composition of the two vials (T=0H and T=2H) was analyzed using GC-MS equipped with a chiral column.

Hydrogenation of Pro-Chiral Substrates with $H_2$ and NiNPs@CNCs

A similar approach was used for the hydrogenation of acetophenone and alpha-tetralone with NiNPs@CNCs. Stock solutions of the substrates were prepared at different concentrations. The substrate (4 ml of the stock solution), NiNPs@CNCs (5 ml) and distilled water (6 ml) were mixed in a small vial. The solution was stirred for one minute on the vortex. The mixture was placed in the PARR reactor under $H_2$ pressure. Aliquots of the product taken at different time periods were analyzed using GC-MS with the cyclohexanol internal standard, following the same procedure as the one described for PdNPs@CNCs.

One differentiating aspect of both NiNPs@CNCs and PdNPs@CNCs versus other catalysts is that they are green catalysts because CNCs originate from an abundant renewable resource. To keep the reaction environmentally-benign, reaction conditions should be as gentle as possible to minimize energy consumption. The hydrogenation reaction with NiNPs@CNCs was thus initially performed at room temperature. However, Ni requires harsher experimental conditions. The pressure was increased from 4 to 40 bars and the reaction time was extended to 24 h, but no reaction took place. Next, the temperature was raised to 75° C. and the reaction was performed at 40 bars, but again no conversion occurred. Positive results were obtained when the reaction was conducted at 75° C. and 75 bars, which was the maximum pressure given by a new hydrogen tank. The temperature could not be increased above 100° C. because water and acetophenone both evaporated within 1 h.

Sample Analysis Using GC-MS

Cyclohexanol was used as an internal standard for all the catalytic tests. This chemical was chosen because of its similar structure and boiling point with the substrates studied: acetophenone, 1-(2-methoxyphenyl)ethanone and alpha-tetralone. Furthermore, cyclohexanol is stable and does not react under the reaction conditions used in this project.

A GC-MS instrument was used to evaluate the catalytic performance of PdNPs@CNCs and NiNPs@CNCs. For each novel reaction, a separate method was developed and optimized to ensure the separation of compounds present in each final product. The new methods were first tested on standard chemicals before the reactions were performed.

Results and Discussion

Hydrogenation of 1-(2-methoxyphenyl)ethanone with PdNPs@CNCs

Figure 13:
FIG. 13 shows the hydrogenation of 1-(2-methoxyphenyl)ethanone with $H_2$ and PdNPs@CNCs.
Figure 14:
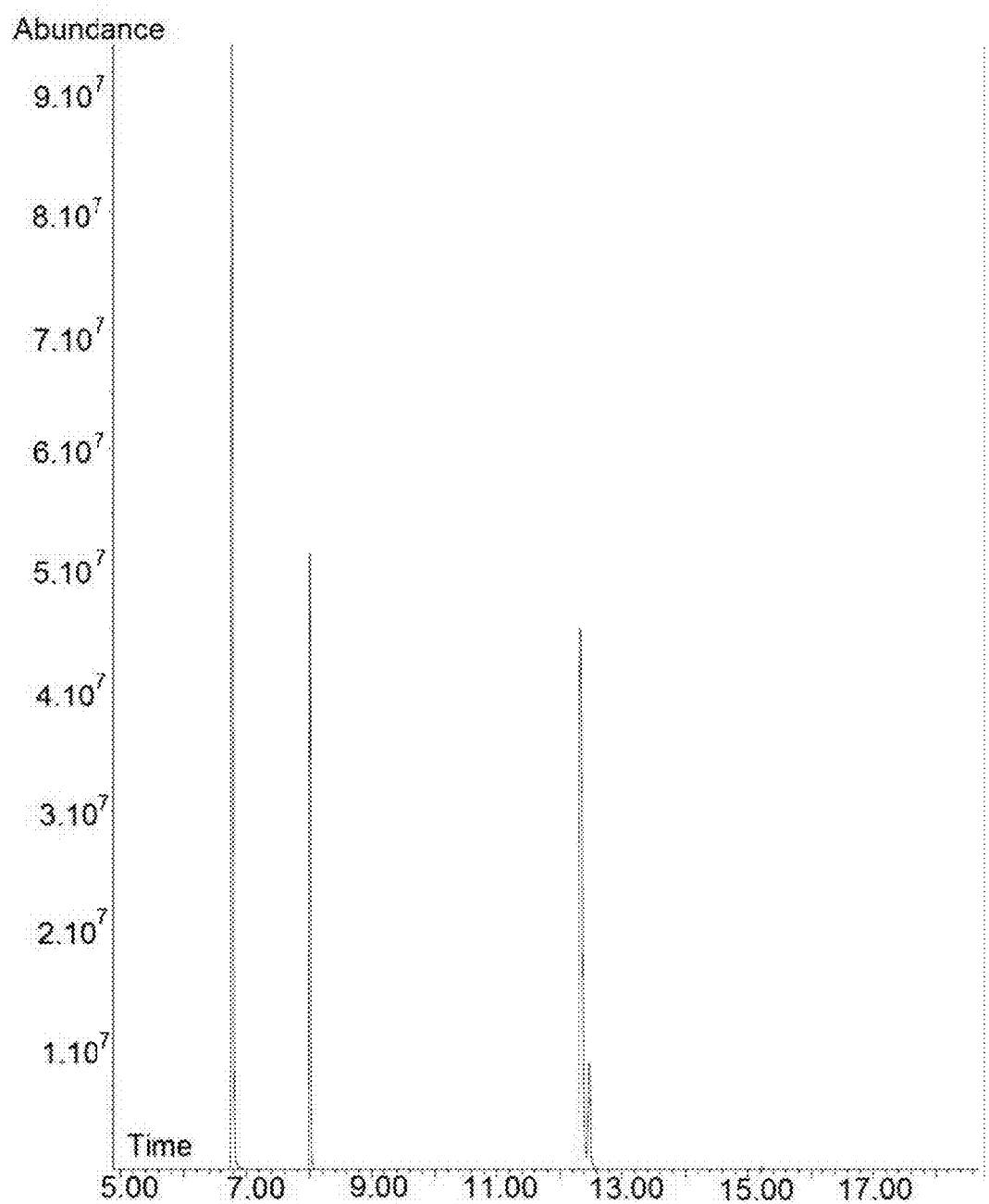
FIG. 14 shows the GC-MS spectrum for the hydrogenation of 1-(2-methoxyphenyl)ethanone with PdNPs@CNCS at 4 bars and room temperature for 2 h.
Figure 15A:
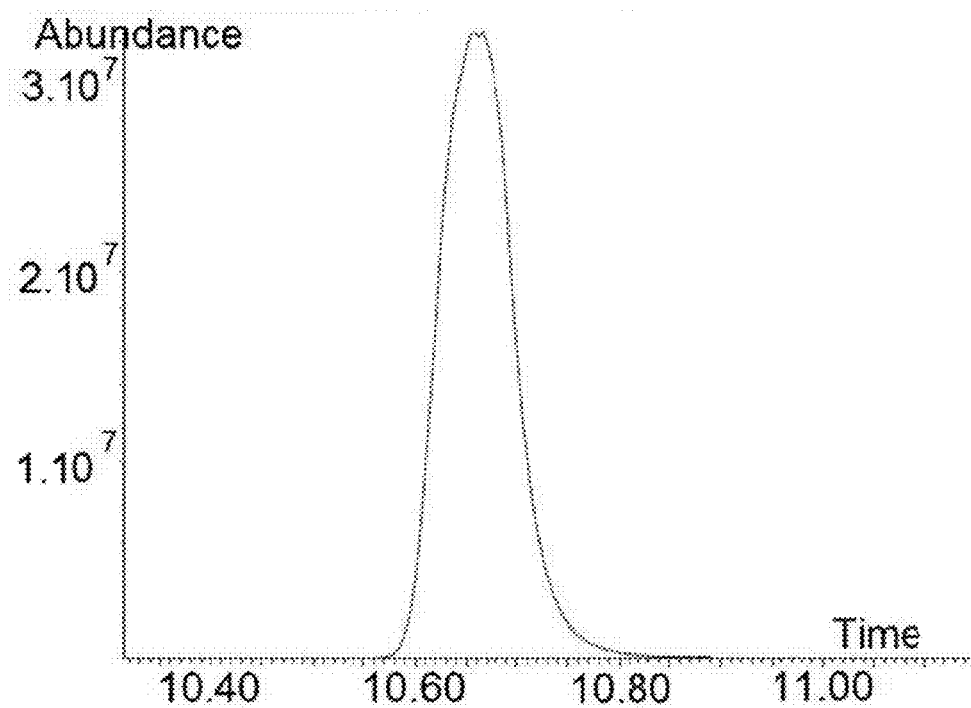
FIG. 15 shows the GC-MS spectra of R and S isomers of 1-(2-methoxyphenyl)ethanol standard: (top left) 165° C. isothermal, (top right) 150° C. isothermal, (bottom left) 140° C. isothermal, (bottom right) 130° C. isothermal.
Figure 15B:
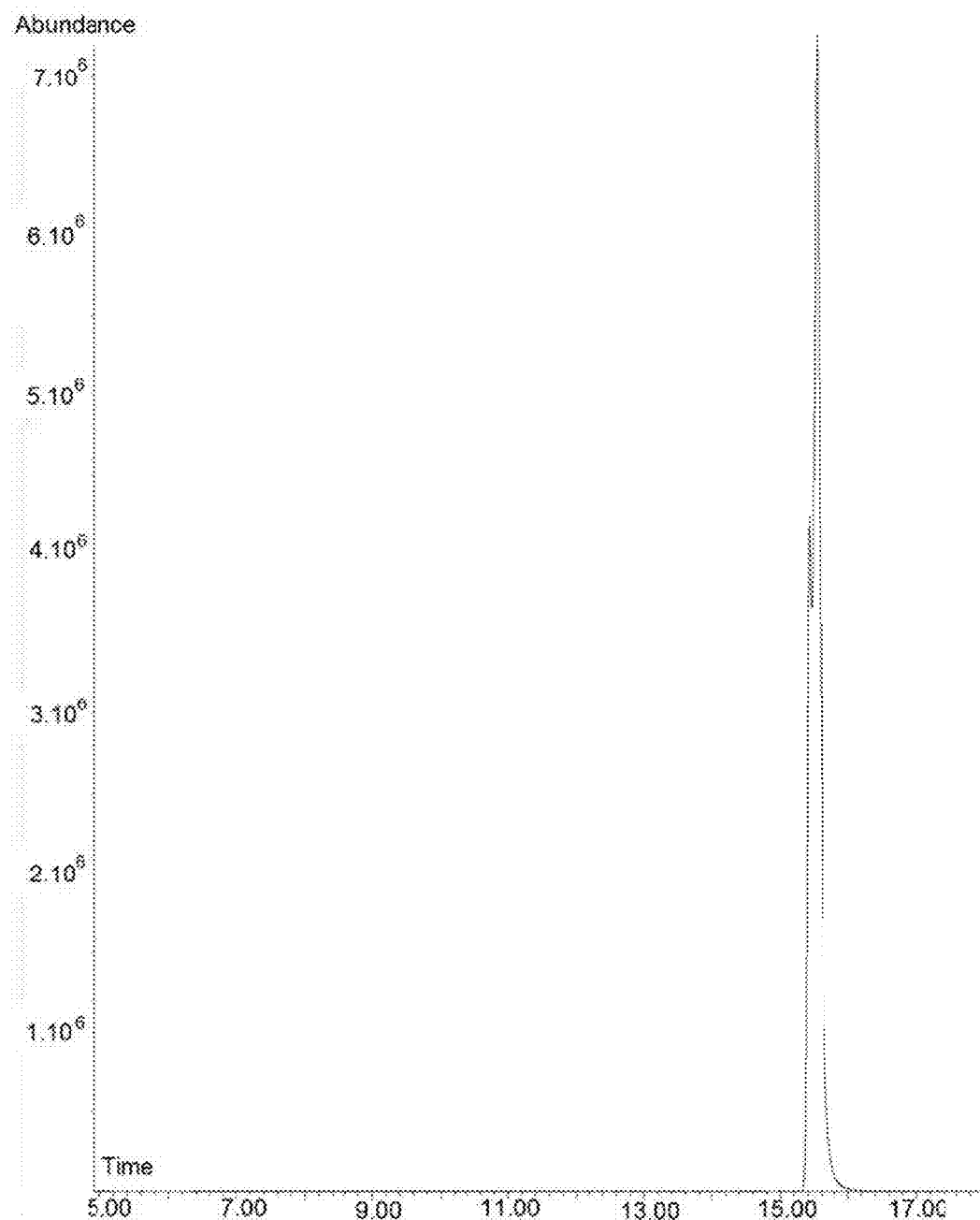
Figure 15C:
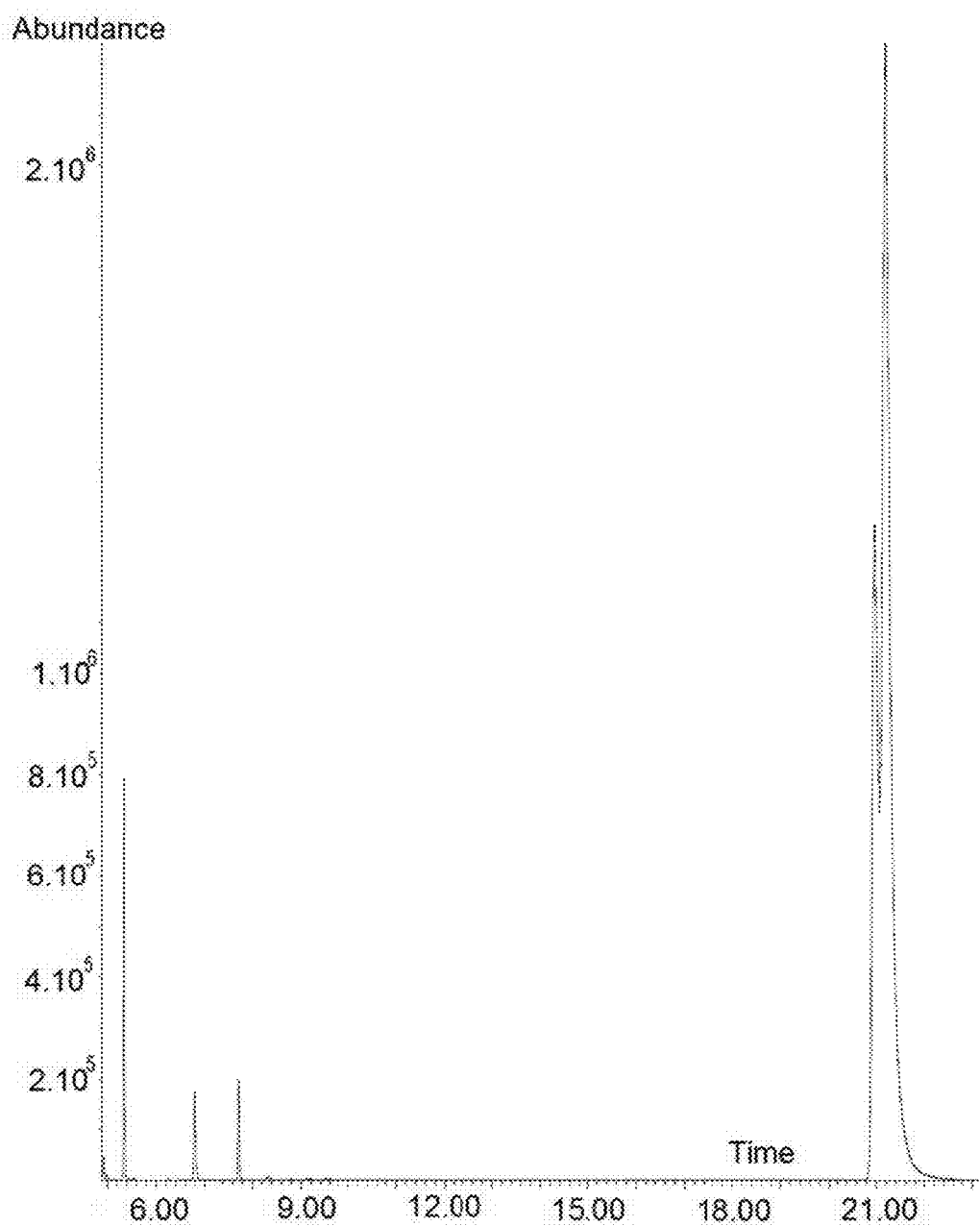
Figure 15D:
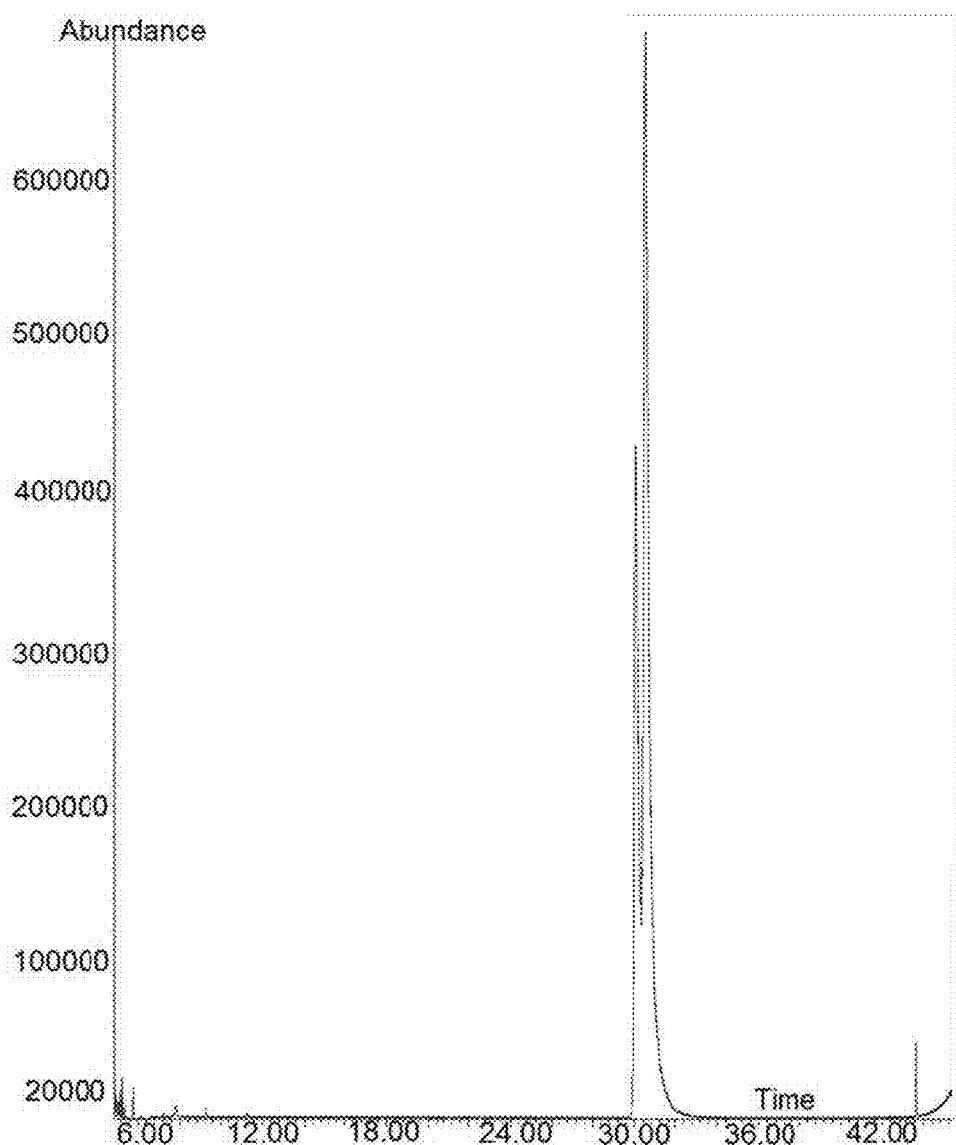

The hydrogenation reaction of 1-(2-methoxyphenyl)ethanone was performed under mild conditions: 4 bars $H_2$ pressure and room temperature. The ketone group was first reduced to an alcohol and then to an alkane according to FIG. 13. Aliquots of the reaction mixture taken after 0, 1 and 2 hours were analyzed on the GC-MS. The spectrum of the first sample after 2 h is presented in FIG. 14. The results are summarized in Table 2.

TABLE 2

Hydrogenation of 1-(2-methoxyphenyl)ethanone with $H_2$ (4 bars) and PdNPs@CNCs at Room Temperature

| Reaction Time (Hours) | 1-(2-methoxy-phenyl)ethanone | 1-(2-methoxy-phenyl)ethanol | 1-ethyl-methoxybenzene |
| --- | --- | --- | --- |
| 1 | 20.6% | 60.3% | 19.2% |
| 2 | 10.6% | 63.6% | 25.8% |
| 2 | 15.6% | 59.2% | 25.3% |
| 2 | 8.4% | 60.2% | 31.5% |

The triplicates were obtained within a 2-month interval between each replica, which illustrates their consistency and reproducibility. The rate of the two reactions is similar since the concentration of the reactant decreased by 9.1% and the concentration of 1-ethyl-2-methoxybenzene increased by 8.3% when the reaction time was doubled from 1 h to 2 h while the concentration of the intermediary product, 1-(2-methoxyphenyl)ethanol, was almost constant (slight increase of 0.7%). By further increasing the reaction time, the formation of 1-ethyl-2-methoxybenzene would be favored.

Enantiomeric Excess of 1-(2-methoxyphenyl)ethanol

To achieve enantiomeric selectivity with CNCs, the first step consisted in separating two enantiomers using GC-MS. Various methods were tested with a reference sample of 1-(2-methoxyphenyl)ethanone, using different combinations of temperature ramps and holding times, but no enantioselective separation was achieved. The spectra of 1-(2-methoxyphenyl)ethanol standard using isothermal temperatures of 165° C., 150° C., 140° C. and 130° C. on the GC-MS are presented in FIG. 15. Clearly, the peak separation increases as the isothermal oven temperature decreases.

This successful strategy for separating enantiomers on the GC-MS was applied to the product for the hydrogenation reaction of 1-(2-methoxyphenyl)ethanone. The peak areas decreased significantly using isothermal oven temperature compared to the previous methods used. However, the R and S enantiomers were separated and the enantiomeric excess of the peak areas was found to be 29.4%. The results for the duplicates are presented in Table 3.

TABLE 3

Enantiomeric Ratio of 1-(2-methoxyphenyl)ethanol After Hydrogenation of 1-(2-methoxyphenyl)ethanone with $H_2$ (4 bars) and PdNPs@CNCs at Room Temperature

| Sample | Enantiomer 1 | Enantiomer 2 |
| --- | --- | --- |
| 1 | 36.0% | 64.0% |
| 2 | 34.6% | 65.4% |

Hydrogenation of Alpha-Tetralone with PdNPs@CNCs

Figure 16:
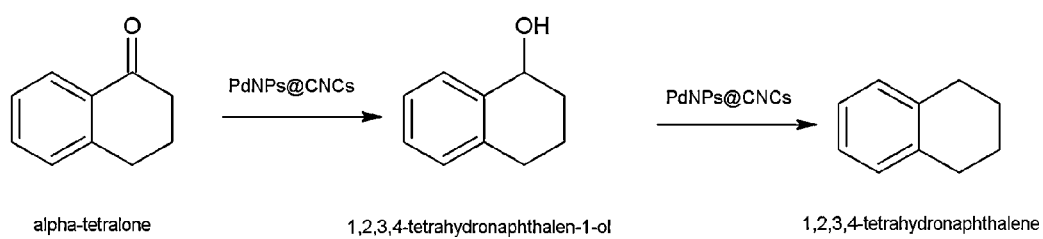
FIG. 16 shows the hydrogenation of alpha-tetralone with $H_2$ and PdNPs@CNCs.
Figure 17:
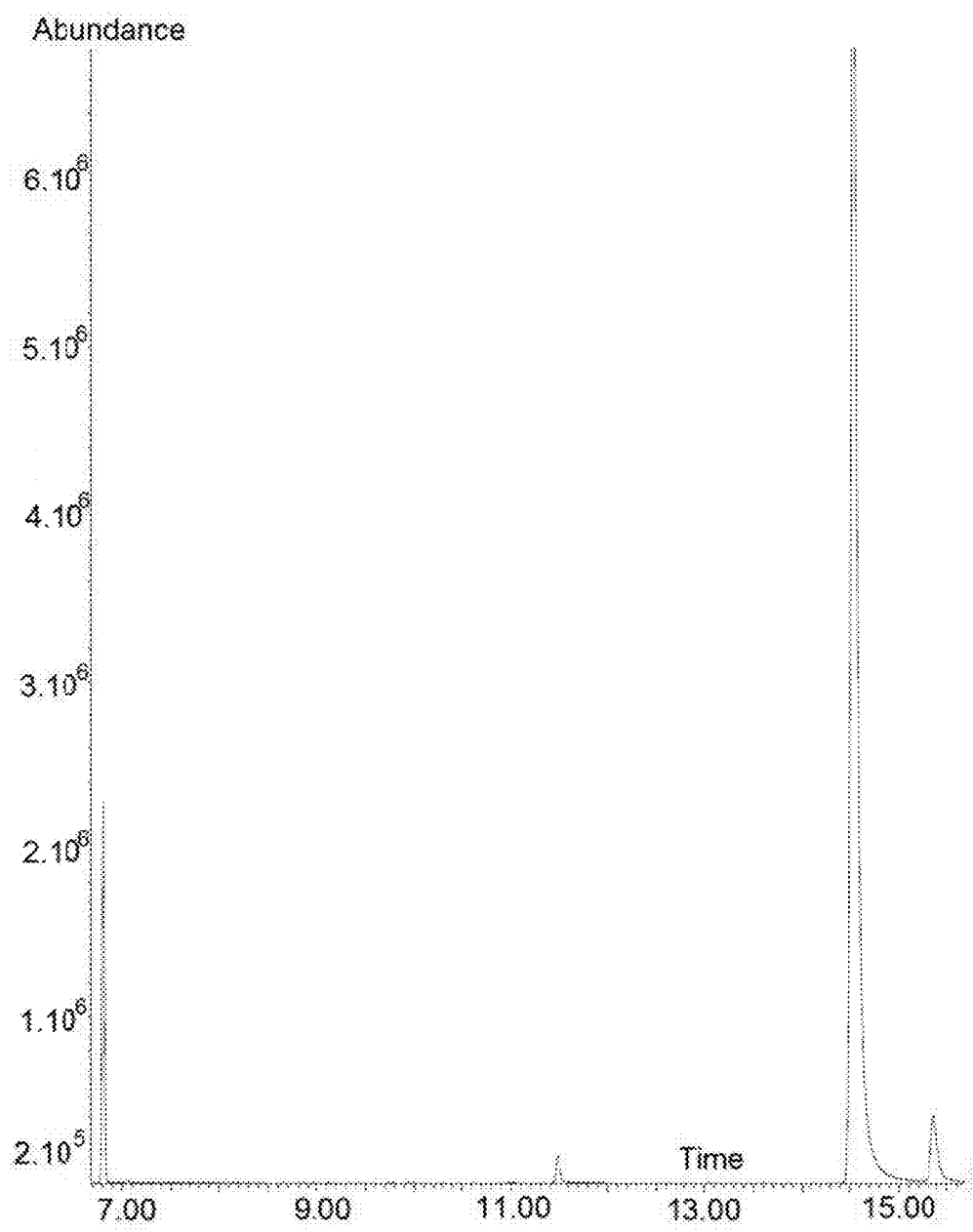
FIG. 17 shows the GC-MS spectrum for the hydrogenation of alpha-tetralone with PdNPs@CNCS at 4 bars and room temperature for 2 h.

The hydrogenation reaction of alpha-tetralone was performed under mild conditions: 4 bars $H_2$ pressure and room temperature. Similarly to 1-(2-methoxyphenyl)ethanone, the ketone group was first reduced to an alcohol and then to an alkane according to the scheme shown in FIG. 16. The spectrum of the third run is presented in FIG. 17. The results are summarized in Table 4.

TABLE 4

Hydrogenation of alpha-tetralone with $H_2$ (4 bars) and PdNPs@CNCs at Room Temperature for 2 hours

| Run | Alpha-tetralone | 1,2,3,4-tetrahydronaphthalen-1-ol | 1,2,3,4-tetrahydronaphthalene |
| --- | --- | --- | --- |
| 1 | 6.2% | 87.7% | 6.1% |
| 2 | 2.0% | 91.1% | 6.9% |
| 3 | 4.9% | 86.7% | 8.4% |
| Average of 1-3 | 4.4% | 88.5% | 7.1% |

Excellent conversion of alpha-tetralone to 1,2,3,4-tetrahydronaphthalen-1-ol was obtained (88.5%) with a small amount (7.1%) being further reduced to 1,2,3,4-tetrahydronaphthalene. The results for the three runs, taken over a 5-week interval, were consistent.

Hydrogenation of Acetophenone with NiNPs@CNCs

Figure 18:
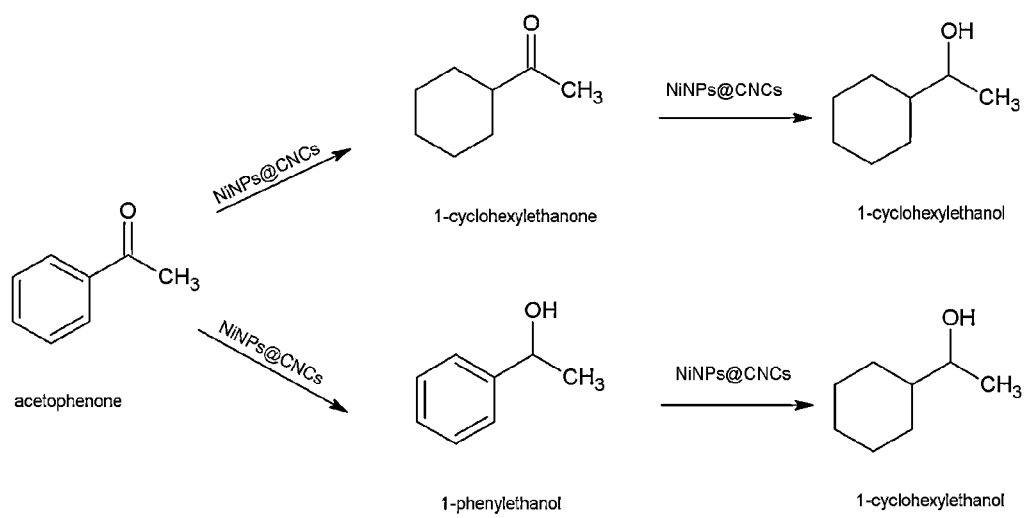
FIG. 18 shows the hydrogenation of acetophenone with $H_2$ and NiNPs@CNCs.

Conversion of acetophenone by hydrogenation was performed at 75° C. and 75 bars of $H_2$ pressure. Acetophenone was reduced to three different products illustrated in FIG. 18, which shows the strength of the NiNPs@CNCs catalyst as a reducing agent. The results for this reaction are summarized in Table 5.

TABLE 5

Hydrogenation of acetophenone with $H_2$ (75 bars) and NiNPs@CNCs

| Reaction Time (Hours) | Temperature (° C.) | Acetophenone | 1-Cyclohexyl ethanol | 1-Cyclohexyl ethanone | 1-phenyl ethanol |
| --- | --- | --- | --- | --- | --- |
| 1 | 20 | 100% | | | |
| 2 | 20 | 100% | | | |
| 18 | 20 | 96.45% | 2.51% | 1.24% | 0.16% |
| 1 | 75 | 99.78% | 0.05% | 0.17% | |
| 2 | 75 | 99.75% | 0.09% | 0.16% | |
| 18 | 75 | 93.19% | 0.72% | 0.55% | 5.55% |
| 21 | 75 | 99.61% | 0.16% | 0.23% | |
| 18 | 75 | 99.93% | 0.03% | 0.04% | |
| 41 | 75 | 99.92% | 0.03% | 0.06% | |

Conversion of acetophenone to the three products was relatively low, with a maximum of 6.81% after 18 h at 75° C.

The NiNPs@CNCs catalyst is a stronger reducing agent than PdNPs@CNCs because it performed arene hydrogenation. The hydrogenation reaction of acetophenone with PdNPs@CNCs only produced 1-phenylethanol and ethylbenzene, leaving the aromatic ring intact. Arene hydrogenation is more difficult to perform than the reduction of a ketone group to an alcohol.

Hydrogenation of Alpha-Tetralone with NiNPs@CNCs

Figure 19:
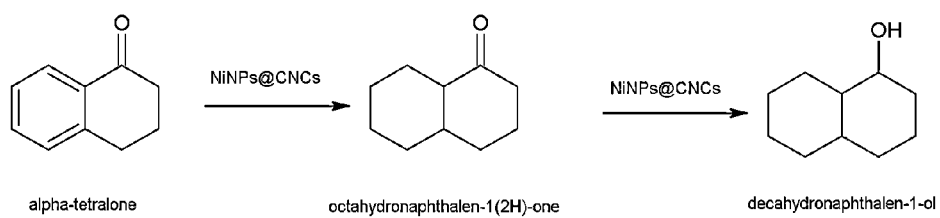
FIG. 19 shows the hydrogenation of alpha-tetralone with $H_2$ and NiNPs@CNCs.

Once hydrogenation of acetophenone with NiNPs@CNCs was successfully performed for the first time, other substrates were tested. No reaction occurred with 1-(2-methoxyphenyl) ethanone. Conversely, the results obtained with alpha-tetralone exceeded expectations. The reaction schematic is presented in FIG. 19 and the results of the successful reaction are compiled in Table 6.

TABLE 6

Hydrogenation of Alpha-Tetralone with $H_2$ (75 bars) and NiNPs@CNCs for 24 hours at 75° C.

| Alpha-tetralone | Octahydronaphthalen-1(2H)-one | Decahydronaphthalen-1-ol |
|---|---|---|
| 0% | 59.2% | 40.8% |

As was noted with the hydrogenation of acetophenone with NiNPs@CNCs, the nickel catalyst favours arene hydrogenation over ketone reduction. The aromatic ring in alpha-tetralone was first reduced, before the ketone group was converted to an alcohol. The reactant was completely converted to the two products after 24 h at 75° C. and 75 bars.

Figure 20:
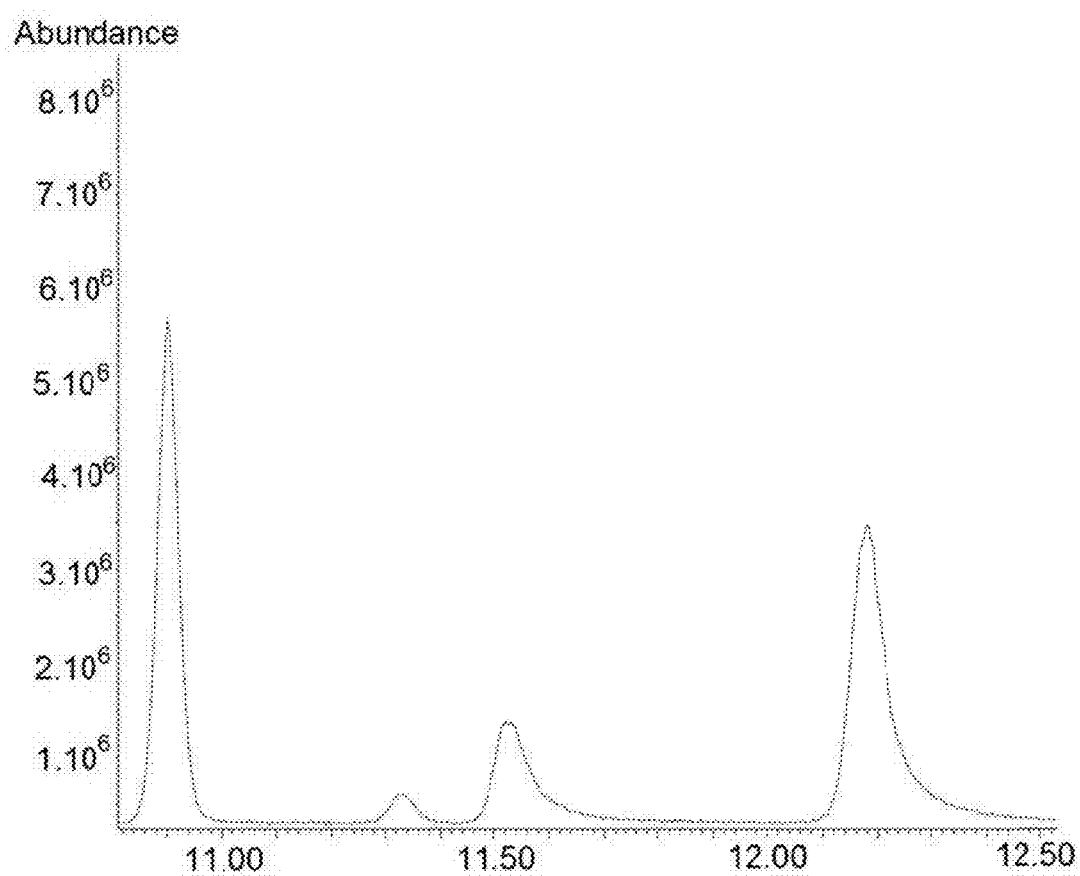
FIG. 20 shows the GC-MS spectrum for the hydrogenation of alpha-tetralone with NiNPs@CNCs at 75 bars and 75° C. for 24 h.

The most striking result for this reaction was that two clearly distinguishable peaks were obtained for decahydronaphthalen-1-ol on the GC-MS, suggesting that the R and S enantiomers were successfully separated. Again, an isothermal method was used on the GC-MS instrument to separate the two enantiomers. The spectrum is presented in FIG. 20. The enantiomeric excess of the two enantiomers was approximately 50%. This result is remarkable considering that no action was taken to favour one enantiomer over the other in the experimental procedure.

CONCLUSION

PdNPs@CNCs catalyst was tested with two new pro-chiral substrates, namely 1-(2-methoxyphenyl)ethanone and alpha-tetralone. The hydrogenation reaction of these two compounds with PdNPs@CNCs was successfully performed under mild conditions: 4 bars $H_2$ pressure and room temperature for 2 h. Excellent conversion rates of 88.5% for 1-(2-methoxyphenyl)ethanone and 95.6% for alpha-tetralone were obtained.

A hydrogenation reaction using Ni@CNCs as a catalyst was successfully performed for the first time with acetophenone and alpha-tetralone. This novel catalyst proved to be a stronger reducing agent compared to PdNPs@CNCs. Arene hydrogenation was favoured over reduction of the ketone group for both substrates. When PdNPs@CNCs was used to catalyze a reaction, the aromatic ring remained intact.

The NiNPs@CNCs catalyst also required harsher experimental conditions. The reactions were conducted at 75 bars of $H_2$ pressure and 75° C. for a minimum of 18 h. Excellent conversion (100%) was achieved for alpha-tetralone. With acetophenone, the hydrogenation reaction was reproducible, but lower conversion was obtained, with a maximum of 6.81%.

CNCs were used to perform enantioselective catalysis. PdNPs@CNCs was used to reduce the ketone group on 1-(2-methoxyphenyl)ethanone and alpha-tetralone to an alcohol, thereby creating a chiral center. The R and S enantiomers of 1-(2-methoxyphenyl)ethanol were separated using an isothermal method on the GC-MS with an enantiomeric excess of 29.4%.

The successful separation of the two isomers in decahydronaphthalen-1-ol during the hydrogenation of alpha-tetralone with NiNPs@CNCs confirms that CNCs can achieve enantioselective catalysis. Moreover, the enantiomeric excess for this reaction was approximately 50% and the two peaks were clearly distinguishable on the spectrum. Since enantioselectivity was achieved with two types of metal nanoparticles (Pd and $N_1$), one may conclude that CNCs are an effective support for enantioselective catalysis The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

K. R. Reddy, N. S. Kumar, P. S. Reddy, B. Sreedhar and M. L. Kantam, J. Mol. Catal. A: Chem., 2006, 252, 12-16.

K. R. Reddy, N. S. Kumar, B. Sreedhar and M. L. Kantam, J. Mol. Catal. A: Chem., 2006, 252, 136-141.

Y. Xu, L. Zhang and Y. C. Cui, J. Appl. Polym. Sci., 2008, 110, 2996-3000.

A. Cyganiuk, R. Klimkiewicz, A. Olejniczak and J. P. Lukaszewicz, Carbon, 2010, 48, 99-106.

Y. Habibi, L. A. Lucia and O. J. Rojas, Chem. Rev., 2010, 110, 3479-3500.

R. R. Lahiji, X. Xu, R. Reifenberger, A. Raman, A. Rudie and R. J. Moon, Langmuir, 2010, 26, 4480-4488.

S. J. Eichhorn, C. A. Baillie, N. Zafeiropoulos, L. Y. Mwaikambo, M. P. Ansell, A. Dufresne, K. M. Entwistle, P. J. Herrera-Franco, G. C. Escamilla, L. Groom, M. Hughes, C. Hill, T. G. Rials and P. M. Wild, J. Mater. Sci., 2001, 36, 2107-2131.

D. Klemm, B. Heublein, H. P. Fink and A. Bohn, Angew. Chem., Int. Ed., 2005, 44, 3358-3393.

S. M. Mukherjee and H. J. Woods, Biochim. Biophys. Acta, 1953, 10, 499-511.

J. Araki, M. Wada, S. Kuga and T. Okano, Colloids Surf., A, 1998, 142, 75-82.

D. Bondeson, A. Mathew and K. Oksman, Cellulose, 2006, 13, 171-180.

S. Elazzouzi-Hafraoui, Y. Nishiyama, J. L. Putaux, L. Heux, F. Dubreuil and C. Rochas, Biomacromolecules, 2008, 9, 57-65.

J. F. Revol, H. Bradford, J. Giasson, R. H. Marchessault and D. G. Gray, Int. J. Biol. Macromol., 1992, 14, 170-172.

K. Oksman, A. P. Mathew, D. Bondeson and I. Kvien, Compos. Sci. Technol., 2006, 66, 2776-2784.

E. D. Cranston and D. G. Gray, Biomacromolecules, 2006, 7, 2522-2530.

R. Marchessault, F. F. Morehead and M. J. Koch, J. Colloid Sci., 1961, 16, 327-344.

J. F. Revol, L. Godbout and D. G. Gray, J. Pulp Pap. Sci., 1998, 24, 146-149.

Y. Shin, J. M. Blackwood, I. T. Bae, B. W. Arey and G. J. Exarhos, Mater. Lett., 2007, 61, 4297-4300.

Y. Shin, I.-T. Bae, B. W. Arey and G. J. Exarhos, Mater. Lett., 2007, 61, 3215-3217.

Y. Shin, I. T. Bae, B. W. Arey and G. J. Exarhos, J. Phys. Chem. C, 2008, 112, 4844-4848.
K. B. Medrzycka, Colloid Polym. Sci., 1991, 269, 85-90.
P. Klufers and T. Kunte, Chem.—Eur. J., 2003, 9, 2013-2018.
K. Pirkkalainen, K. Leppanen, U. Vainio, M. A. Webb, T. Elbra, T. Kohout, A. Nykanen, J. Ruokolainen, N. Kotelnikova and R. Serimaa, Eur. Phys. J. D, 2008, 49, 333-342.
C. M. Cirtiu, H. O. Hassani, N. A. Bouchard, P. A. Rowntree and H. Menard, Langmuir, 2006, 22, 6414-6421.
H. Z. Liu, T. Jiang, B. X. Han, S. G. Liang and Y. X. Zhou, Science, 2009, 326, 1250-1252.
A. K. Talukdar, K. G. Bhattacharyya and S. Sivasanker, Appl. Catal., A, 1993, 96, 229-239.
K. A. Mahmoud, K. B. Male, S. Hrapovic, J. H. T. Luong, *ACS Appl. Mater. Interfaces,* 2009, 1 (7), pp 1383-1386
Moon, R. J.; Martini, A.; Nairn, J.; Simonsen, J.; Youngblood, J., *Chemical Society Reviews* 2011, 40 (7), 3941-3994.
Klemm, D.; Kramer, F.; Moritz, S.; Lindstrom, T.; Ankerfors, M.; Gray, D.; Dorris, A., *Angew Chem Int Ed Engl* 2011, 50 (24), 5438-66.
Hasani, M.; Cranston, E. D.; Westman, G.; Gray, D. G., *Soft Matter* 2008, 4 (11), 2238-2244.
Peng, B. L.; Dhar, N.; Liu, H. L.; Tam, K. C., *The Canadian Journal of Chemical Engineering* 2011, 89 (5), 1191-1206.
Denisov, A. Y.; Kloser, E.; Gray, D. G.; Mittermaier, A. K., *J. Biomol. NMR* 2010, 47, 195-204.
Ghanem, A., *Analytical Chemistry Insights* 2007, 2, 75-80.
"Enantioselective GC Columns" *Chiral Separations*, N.p., 2011. Web. 29 Nov. 2011. <http://chiral-separations.com/images/6/69/ApplicationGuide-ChiralSeparations_828.pdf>.
Schurig, V., *Trends in Analytical Chemistry* 2002, 21, 647-661.
Dykeman, R. R.; Yan, N., Scopelliti, R., Dyson, P. J., *Inorg. Chem.* 2011, 50, 717-719

The invention claimed is:

1. A catalyst comprising metal nanoparticles supported on nanocrystalline cellulose.

2. The catalyst of claim 1, wherein the metal nanoparticles are comprised of at least one of the following metals: palladium, nickel, ruthenium, platinum, or silver.

3. The catalyst of claim 2, wherein the metal nanoparticles are nickel nanoparticles.

4. The catalyst of claim 2, wherein the metal nanoparticles are palladium nanoparticles.

5. The catalyst of claim 4, wherein the metal nanoparticles have a diameter size range from about 2 nm to about 10 nm.

6. The catalyst of claim 5, wherein the metal nanoparticles have a diameter size range of about 2 nm to about 4 nm.

7. The catalyst of claim 6, wherein the loading of palladium on the nanocrystalline cellulose is in a range of about 0.5 weight % to about 5 weight %.

8. The catalyst of claim 1, wherein the metal nanoparticles are uniformly distributed onto the nanocrystalline cellulose.

9. The catalyst of claim 1, wherein the nanocrystalline cellulose is cellulose nanocrystallites (CNCs).

10. The catalyst of claim 1, wherein the nanocrystalline cellulose is in the form of whiskers having a length in a range of about 100 nm to about 300 nm, and a width of about 5 nm to about 15 nm.

11. The catalyst of claim 1 being a hydrogenation catalyst.

12. The catalyst of claim 1 being a Heck coupling catalyst.

13. A homogeneous catalyst system comprising the catalyst of claim 1 colloidally suspended in a liquid.

14. The catalyst system of claim 13, wherein the liquid is water, or an aqueous mixture of water and acetonitrile.

15. A method for producing the catalyst of claim 1, the method comprising:
   a. mixing an aqueous suspension of nanocrystalline cellulose with an acidic solution of a metal salt at a temperature of about 15° C. to about 25° C.; and
   b. exposing the resulting slurry to dihydrogen pressure in order to reduce the metal salt to a metal nanoparticle at a temperature of about 15° C. to about 25° C.

16. The method of claim 15, wherein the acidic solution of a metal salt is at a pH of about 2.

17. The method of claim 15, wherein the pressure is from about 2 to about 10 bars.

18. The method of claim 15, wherein the metal salt is palladium chloride or nickel chloride.

19. The method claim 17, wherein the pressure is at about 4 bars.

* * * * *